(12) United States Patent
Hochrein et al.

(10) Patent No.: US 8,053,234 B2
(45) Date of Patent: Nov. 8, 2011

(54) INDUCTION OF DENDRITIC CELL DEVELOPMENT WITH MACROPHAGE-COLONY STIMULATING FACTOR (M-CSF)

(75) Inventors: Hubertus Hochrein, Munich (DE); Meredith O'Keeffe, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 272 days.

(21) Appl. No.: 11/790,798

(22) Filed: Apr. 27, 2007

(65) Prior Publication Data

US 2008/0267994 A1    Oct. 30, 2008

(51) Int. Cl.
*C12N 5/071*    (2010.01)
*C12N 5/00*     (2006.01)
*C12N 5/02*     (2006.01)

(52) U.S. Cl. .................................. 435/372; 435/377

(58) Field of Classification Search .................... None
See application file for complete search history.

(56) References Cited

U.S. PATENT DOCUMENTS

| 7,198,948 | B2 | 4/2007 | Steinman |
| 2009/0148405 | A1 | 6/2009 | Hochrein |

FOREIGN PATENT DOCUMENTS

| EP | 0 326 149 A2 | 8/1989 |
| WO | WO2004/020613 A1 | 3/2004 |

OTHER PUBLICATIONS

Koya et al., 2004, Human Gene Ther. vol. 15: 733-748.*
Di Nicola et al., 2004, Clin. Canc. Res. vol. 10: 5381-5390.*
Zhang et al., 2005, Bochem. and Biophys. Res. Com. vol. 330: 1275-1284.*
Bernhard et al., 1995, Can. Res. vol. 55: 1099-1104.*
Nikolic et al., 2003, int. Immunol. vol. 15: 515-524.*
Xu et al. 1997, canc. Viother. Radiopharm. vol. 12: 27-36.*
Tadokoro et al., 2001, Immunol. Letter. vol. 77: 31-38.*
Yamaguchi et al., 1983, Blood vol. 62: 597-601.*
Oliveira et al., 2003, J. Leuk. Biol. vol. 74: 857-867.*
Advani AS. 2005. FLT3 and acute myelogenous leukemia: biology, clinical significance and therapeutic applications. Curr Pharm Des. 11:3449-57.
Barbaroux Jean-Baptiste et al. 2006. Tumor necrosis factor-alpha- and IL-4-independent development of Langerhans cell-like dendritic cells from M-CSF-conditioned precursors. The Journal of Investigative Dermatology, vol. 126, No. 1, 114-120.
Bartocci,A., D.S.Mastrogiannis, G.Migliorati, R.J.Stockert, A.W. Wolkoff, and E.R.Stanley. 1987. Macrophages specifically regulate the concentration of their own growth factor in the circulation. Proc. Natl. Acad. Sci. U. S. A 84:6179-6183.

Bjorck,P. 2001. Isolation and characterization of plasmacytoid dendritic cells from Flt3 ligand and granulocyte-macrophage colony-stimulating factor-treated mice. Blood 98:3520-3526.
Brasel,K., S.T.DE, J.L.Smith, and C.R.Maliszewski. 2000. Generation of murine dendritic cells from flt3-ligand-supplemented bone marrow cultures. Blood 96:3029-3039.
Brawand,P., D.R.Fitzpatrick, B.W.Greenfield, K.Brasel, C.R. Maliszewski, and T.DE Smedt. 2002. Murine plasmacytoid pre-dendritic cells generated from Flt3 ligand-supplemented bone marrow cultures are immature APCs. J. Immunol. 169:6711-6719.
Briard D et al. 2005. Importance of stromal determinants in the generation of dendritic and natural killer cells in the human spleen. Clinical and Experiment Immunology vol. 140, No. 2, 265-273.
Chitu,V. and E.R.Stanley. 2006. Colony-stimulating factor-1 in immunity and inflammation. Curr. Opin. Immunol 18:39-48.
Christensen and Shlomochik. 2007. Regulation of lupus-related autoantibody production and clinical disease by Toll-like receptors. Semin. Immunol. 19: 11-23.
Cremer Isabelle et al. 2002. Long-lived immature dendritic cells mediated by TRANCE-RANK interaction. Blood vol. 100, No. 10, 3646-3655.
D'Amico,A. and L.Wu. 2003. The early progenitors of mouse dendritic cells and plasmacytoid predendritic cells are within the bone marrow hemopoietic precursors expressing Flt3. J. Exp. Med 198:293-303.
Diebold,S.S., M.Montoya, H.Unger, L.Alexopoulou, P.Roy, L.E. Haswell, A.AL Shamkhani, R. Flavell, P.Borrow, and Reis E Sousa. 2003. Viral infection switches non-plasmacytoid dendritic cells into high interferon producers. Nature 424:324-328.
Fogg et al., 2006. A Clonogenic Bone Marrow Progenitor Specific for Macrophages and Dendritic Cells. Science, 311:83-87.
Franchini,M., H.Hefti, S.Vollstedt, B.Glanzmann, M.Riesen, M.Ackermann, P.Chaplin, K. Shortman, and M.Suter. 2004. Dendritic cells from mice neonatally vaccinated with modified vaccinia virus Ankara transfer resistance against herpes simplex virus type I to naive one-week-old mice. J. Immunol. 172:6304-6312.
Gill,M.A., P.Blanco, E.Arce, V.Pascual, J.Banchereau, and A.K. Palucka. 2002. Blood dendritic cells and DC-poietins in systemic lupus erythematosus. Hum. Immunol. 63:1172-1180.

(Continued)

*Primary Examiner* — Amy Juedes
(74) *Attorney, Agent, or Firm* — Law Office of Salvatore Arrigo and Scott Lee, LLP (57) ABSTRACT

A method of inducing dendritic cell (DC) development by administering Macrophage-Colony Stimulating Factor is provided. M-CSF induces DCs to differentiate into subtypes, for example plasmacytoid DCs and conventional DCs. Induction with M-CSF can be achieved in vitro from hematopoietic precursors, such as bone marrow cells, or in vivo. In vitro, M-CSF-derived DCs can be used to produce cytokines and to stimulate other immune response cells. M-CSF can also be used to induce precursor cells removed from an animal to develop into DCs. In addition, these isolated DCs can be exposed to antigens to stimulate a specific immune response when reintroduced into the animal. Treatments for cancers, such as Acute Myeloid Leukemia, and autoimmune diseases such as Systemic Lupus Erythematosus, are also provided in the invention.

8 Claims, 7 Drawing Sheets

OTHER PUBLICATIONS

Gilliet,M., A.Boonstra, C.Paturel, S.Antonenko, X.L.Xu, G.Trinchieri, A.O'Garra, and Y.J.Liu. 2002. The development of murine plasmacytoid dendritic cell precursors is differentially regulated by FLT3-ligand and granulocyte/macrophage colony-stimulating factor. J. Exp. Med 195:953-958.

Graf C, Heidel F, Tenzer S, Radsak MP, Solem FK, Britten CM, Huber C, Fischer T, Wolfel T. 2006. A neoepitope generated by a FLT3 internal tandem duplication (FLT3-ITD) is recognized by leukemia-reactive autologous CD8+ T cells. Blood 109(7):2985-8 Prepublished online Nov. 21, 2006; DOI 10.1182/blood-2006-07-032839.

Guha-Thakurta,N. and J.A.Majde. 1997. Early induction of proinflammatory cytokine and type I interferon mRNAs following Newcastle disease virus, poly [rI:rC], or low-dose LPS challenge of the mouse 1. J Interferon Cytokine Res. 17:197-204.

Hochrein,H., B.Schlatter, M.O'Keeffe, C.Wagner, F.Schmitz, M.Schiemann, S.Bauer, M.Suter, and H.Wagner. 2004. Herpes simplex virus type-1 induces IFN-alpha production via Toll-like receptor 9-dependent and -independent pathways. Proc. Natl. Acad. Sci. U. S. A 101:11416-11421.

Hsu et al. 1996. Vaccination of Patients with B-Cell Lymphoma Using Autologous Antigen-Pulsed Dendritic Cells. Nat. Med. 2:52-58.

Hübel, et al., 2002. Therapeutic use of cytokines to modulate phagocyte function for the treatment of infections diseases: Current status of Granulocyte Colony-Stimulating Factor, Granulocyte-Macrophage Colony-Stimulating Factor, Macrophage Colony-Stimulating Factor, and Interferon-$\gamma$. J. Infect. Dis., 185: 1490-501.

Inaba,K., M.Inaba, N.Romani, H.Aya, M.Deguchi, S.Ikehara, S.Muramatsu, and R.M.Steinman. 1992. Generation of large numbers of dendritic cells from mouse bone marrow cultures supplemented with granulocyte/macrophage colony-stimulating factor. J Exp. Med. 176:1693-1702.

Ishii,K.J. and S.Akira. 2006. Innate immune recognition of, and regulation by, DNA. Trends Immunol 27:525-532.

Itoh,Y., T.Okanoue, S.Sakamoto, K.Nishioji, and K.Kashima. 1997. The effects of prednisolone and interferons on serum macrophage colony stimulating factor concentrations in chronic hepatitis B. J Hepatol. 26:244-252.

Kamps A W A et al. 1999. Role of macrophage colony-stimulating factor in the differentiation and expansion of monocytes and dendritic cells from cd34+ progenitor cells. Medical Oncology, 16(1): 46-52.

Kappelmayer J, Udvardy M, Antal-Szalmas P. 2007. Pgp and FLT3: identification and modulation of two proteins that lead to chemotherapy resistance in acute myeloid leukemia. Curr Med Chem., 14:519-30.

Karsunky,H., M.Merad, A.Cozzio, I.L.Weissman, and M.G.Manz. 2003. Flt3 ligand regulates dendritic cell development from Flt3+ lymphoid and myeloid-committed progenitors to Flt3+ dendritic cells in vivo. J Exp. Med. 198:305-313.

Kreisel,F.H., A.Blasius, D.Kreisel, M.Colonna, and M.Cella. 2006. Interferon-producing cells develop from murine CD31(high)/Ly6C(-) marrow progenitors. Cell Immunol 242:91-98.

Krug,A., S.Rothenfusser, V.Hornung, B.Jahrsdorfer, S.Blackwell, Z.K.Ballas, S.Endres, A.M. Krieg, and G.Hartmann. 2001. Identification of CpG oligonucleotide sequences with high induction of IFN-alpha/beta in plasmacytoid dendritic cells. Eur. J. Immunol. 31:2154-2163.

MacDonald,K.P., V.Rowe, A.D.Clouston, J.K.Welply, R.D.Kuns, J.L.Ferrara, R.Thomas, and G.R. Hill. 2005. Cytokine expanded myeloid precursors function as regulatory antigen-presenting cells and promote tolerance through IL-10-producing regulatory T cells. J. Immunol. 174:1841-1850.

MacDonald,K.P. et al. 2005. The colony-stimulating factor 1 receptor is expressed on dendritic cell s during differentiation and regulates their expansion. J. Immunology, vol. 175, No. 3, 1399-1405.

Maraskovsky,E., K.Brasel, M.Teepe, E.R.Roux, S.D.Lyman, K.Shortman, and H.J.McKenna. 1996. Dramatic increase in the numbers of functionally mature dendritic cells in Flt3 ligand-treated mice: multiple dendritic cell subpopulations identified. J. Exp. Med 184:1953-1962.

McKenna,H.J., K.L.Stocking, R.E.Miller, K.Brasel, S.T.De, E.Maraskovsky, C.R.Maliszewski, D.H. Lynch, J.Smith, B.Pulendran, E.R.Roux, M.Teepe, S.D.Lyman, and J.J.Peschon. 2000. Mice lacking flt3 ligand have deficient hematopoiesis affecting hematopoietic progenitor cells, dendritic cells, and natural killer cells. Blood 95:3489-3497.

Mollah Zia U A et al. 2003. Macrophage colony-stimulating factor in cooperation with transforming growth factor-beta1 induces the differentiation of CD34+ hematopoietic progenitor cells into Langerhans cells under serum-free conditions without granulocyte-macrophage colony-stimulating factor. The Journal of Investigative Dermatology, vol. 120, No. 2, 256-265.

Naik,S.H., A.I.Proietto, N.S.Wilson, A.Dakic, P.Schnorrer, M.Fuchsberger, M.H.Lahoud, M. O'Keeffe, Q.X.Shao, W.F.Chen, J.A.Villadangos, K.Shortman, and L.Wu. 2005. Cutting edge: generation of splenic CD8+ and CD8- dendritic cell equivalents in Fms-like tyrosine kinase 3 ligand bone marrow cultures. J. Immunol. 174:6592-6597.

O'Keeffe,M., H.Hochrein, D.Vremec, I.Caminschi, J.L.Miller, E.M. Anders, L.Wu, M.H.Lahoud, S. Henri, B.Scott, P.Hertzog, L.Tatarczuch, and K.Shortman. 2002. Mouse plasmacytoid cells: long-lived cells, heterogeneous in surface phenotype and function, that differentiate into CD8(+) dendritic cells only after microbial stimulus. J. Exp. Med 196:1307-1319.

O'Keeffe,M., H.Hochrein, D.Vremec, J.Pooley, R.Evans, S.Woulfe, and K.Shortman. 2002. Effects of administration of progenipoietin 1, Flt-3 ligand, granulocyte colony-stimulating factor, and pegylated granulocyte-macrophage colony-stimulating factor on dendritic cell subsets in mice. Blood 99:2122-2130.

Omatsu,Y., T.Iyoda, Y.Kimura, A.Maki, M.Ishimori, N.Toyama-Sorimachi, and K.Inaba. 2005. Development of Murine Plasmacytoid Dendritic Cells Defined by Increased Expression of an Inhibitory NK Receptor, Ly49Q. J Immunol 174:6657-6662.

Pulendran,B., J.Banchereau, S.Burkeholder, E.Kraus, E.Guinet, C.Chalouni, D.Caron, C. Maliszewski, J.Davoust, J.Fay, and K.Palucka. 2000. Flt3-ligand and granulocyte colony-stimulating factor mobilize distinct human dendritic cell subsets in vivo. J. Immunol. 165:566-572.

Sallusto,F. and A.Lanzavecchia. 1994. Efficient presentation of soluble antigen by cultured human dendritic cells is maintained by granulocyte/macrophage colony-stimulating factor plus interleukin 4 and downregulated by tumor necrosis factor alpha. J Exp. Med. 179:1109-1118.

Scheicher,C., M.Mehlig, R.Zecher, and K.Reske. 1992. Dendritic cells from mouse bone marrow: in vitro differentiation using low doses of recombinant granulocyte-macrophage colony-stimulating factor. J Immunol Methods 154:253-264.

Shortman,K. and Y.J.Liu. 2002. Mouse and human dendritic cell subtypes. Nat. Rev. Immunol. 2:151-161.

Spies,B., H.Hochrein, M.Vabulas, K.Huster, D.H.Busch, F.Schmitz, A.Heit, and H.Wagner. 2003. Vaccination with plasmid DNA activates dendritic cells via Toll-like receptor 9 (TLR9) but functions in TLR9-deficient mice. J. Immunol. 171:5908-5912.

Steinman,R.M. and K.Inaba. 1999. Myeloid dendritic cells. J Leukoc. Biol. 66:205-208.

Stoll ML, Price KD, Silvin CJ, Jiang F, Gavalchin J. 2007. Immunization with peptides derived from the idiotypic region of lupus-associated autoantibodies delays the development of lupus nephritis in the (SWRxNZB)F(1) murine model.J Autoimmun. 29(1):30-7 (Epub ahead of print Apr. 2007).

Sweet,M.J., C.C.Campbell, D.P.Sester, D.Xu, R.C.McDonald, K.J. Stacey, D.A.Hume, and F.Y.Liew. 2002. Colony-stimulating factor-1 suppresses responses to CpG DNA and expression of toll-like receptor 9 but enhances responses to lipopolysaccharide in murine macrophages. J Immunol 168:392-399.

Takashima et al., 1995. Colony-stimulating Factor-1 Secreted by Fibroblasts Promotes the Growth of Dendritic Cell Lines XS Series) Derived From Murine Epidermis. J. Immunol., 154:5128-35.

Vollstedt, S., M.O'Keeffe, B.Ryf, B.Glanzmann, H.Hochrein, and M.Suter. 2006. The long-term but not the short-term antiviral effect of IFN-alpha depends on Flt3 ligand and pDC. Eur. J. Immunol. 36:1231-1240.

Vremec, D., G.J.Lieschke, A.R.Dunn, L.Robb, D.Metcalf, and K.Shortman. 1997. The influence of granulocyte/macrophage colony-stimulating factor on dendritic cell levels in mouse lymphoid organs. Eur. J. Immunol. 27:40-44.

Zheng R, Small D. 2005. Mutant FLT3 signaling contributes to a block in myeloid differentiation. Leuk Lymphoma. 46:1679-87.

Kim et al., Macrophage Colony-Stimulating Factor Can Modulate Immune Responses and Attrct Dendritic Cells in Vivo, Human Gene Therapy 11:305-311 (2000).

Misawa et al., Administration of macrophage colony-stimulating factor mobilized both CD11b+CD11c cells and NK1.1+ cells into peripheral cells, International Immunopharmacology 4:791-803 (2004).

Chen et al., Thrombopoietin cooperates with FLT3-ligand in the generation of plasmacytoid dendritic cell precursors from human hematopoietic progenitors, Blood 103:2547-2553 (2004).

Bangert et al., Immunopathologic Features of Allergic Contact Dermatitis in Humans: Participation of Plasmacytoid Dendritic Cells in the Pathogenesis of the Disease? J Invest Dermatol 121:1409-1418 (2003).

Wood et al., Human Dendritic Cells and Macrophages: In Situ Immunophenotypic Definition of Subsets That Exhibit SpecfiJc Morphologic and Microenvironmental Characteristics, Am J Pathol 119:73-82 (1985).

MacDonald et al., Characterization of human blood dendritic cell subsets, Blood 100:4512-4520 (2002).

* cited by examiner

FLKO enriched spleen DC

A

Control FLKO

M-CSF Treated FLKO

INDUCTION OF DENDRITIC CELL DEVELOPMENT WITH MACROPHAGE-COLONY STIMULATING FACTOR (M-CSF)

BACKGROUND OF THE INVENTION

This invention relates to methods of inducing dendritic cell formation and methods of using induced dendritic cells as therapeutic agents.

Dendritic cells (DCs) are important decision makers within the immune system. For example, DCs initiate adaptive immune responses such as antibody production and killer cell formation. DCs also direct the quantity and quality of immune responses, for example determining whether an allergic, inflammatory, or tolerogenic immune response is to be mounted.

Many phenotypically and functionally distinct subsets of DCs exist (1). Though they are rare in the blood and immune organs, DCs include two major subgroups of different subsets, the plasmacytoid DCs (pDCs) and the conventional DCs (cDCs) (2). The cDCs in mouse include at least 3 subsets: $CD4^+CD8^-$, $CD4^+CD8^-$ and $CD4^-CD8^-$. The $CD8^+$ cDCs express the surface marker $CD8\alpha\alpha$ and are the most important cells for cross-presentation of antigens, which allows for killer cell induction against viral infection. The CD8+ cDCs can also produce large amounts of of interleukin-12, an essential cytokine for inflammatory immune responses. The CD8– cDC populations are known to produce large amounts of chemokines and to be better at MHCII presentation of antigens to T cells. pDCs are anti-viral cells, that produce large amounts of the anti-viral and immune protecting cytokines, including type I Interferons (IFN-I) in response to viral DNA or viral RNA.

Like other immune cells, DCs develop from haematopoietic stem cells and later stage precursors under the influence of growth factors and cytokines. Granulocyte-Macrophage-Colony Stimulating Factor (GM-CSF) induces haematopoietic precursor cells and monocytes to develop into DCs, called GM-DCs (3-5). GM-DCs are not the majority of steady state DC subsets in lymphoid organs, though, since mice deficient for either GM-CSF or the GM-CSF receptor do not demonstrate much impairment in DC numbers (6). However, application of stabilized GM-CSF to mice in vivo results in increased levels of $CD8^-$ cDCs, but not pDCs (10). Moreover, GM-CSF has been shown to block generation of pDCs in vitro (7).

Fms-like-Tyrosine-Kinase 3-Ligand (FL) also induces development of DCs, including both cDCs and pDCs, from bone marrow (BM) precursor cells (8,9), both in vitro and in vivo (10-13). The role of FL in development of DCs (called FL-DCs) has been definitively demonstrated by the drastically reduced number of both pDCs (9) and cDCs (14) in the lymphoid organs of mice deficient in FL (FLKO).

Ex vivo isolated or FL-generated pDCs respond to direct stimulation via the Toll like receptors (TLR) 7 and 9 and their respective ligands, RNA and DNA, by producing high levels of Interferon-alpha (IFN-α). Other cell types, including cDCs, can be induced to produce IFN-α in response to active viruses or transfected DNA or RNA. IFN-α production by cDCs, though, is mediated via TLR7 and TLR9 independent pathways, including PKR, RIG-I, MDA5 and TLR-3 and as yet unidentified cytoplasmic DNA-recognition complexes (15-17). Thus, pDCs are the only cells that employ TLR7 and 9 for the high level production of IFN-α. Furthermore, certain nucleic acid molecules, such as CpG-motif containing oligonucleotides (CpG-ODN A-type), induce extremely high levels of IFN-α solely in pDCs (18). Therefore, IFN-α production in response to A-type CpG-ODN is a functional test for the presence of pDCs in mixed cell populations (17).

From studies employing GFP encoded downstream of the receptor for Macrophage Colony Stimulating Factor (M-CSF; also called CSF-1), it is clear that during differentiation of pDCs and cDC subsets the M-CSF receptor is transcribed (26). In addition, there is a report that mice deficient in M-CSF (op/op mice) have reduced numbers of DC subsets (26). Furthermore, DCs and macrophages may develop from a common progenitor cell (41). Other reports show that some DCs, though not pDCs, develop under the influence of a combination of growth factors, including M-CSF (42). Nevertheless, while GM-CSF and FL have been shown to induce development of DCs, M-CSF has always been considered to induce development of monocytes and differentiation of macrophages, not DCs (34).

The effect of M-CSF as a therapeutic treatment has previously been investigated, though in limited situations, such as in the treatment of invasive fungal infections (39). It is not known if the patients treated with M-CSF displayed any changes in their DCs.

An increase in the number of DCs could be therapeutic in certain situations. For instance, more DCs would be helpful in fighting infections in neonatal individuals. Similarly, individuals who suffer from HIV infection, certain cancers, allergies, have received transplants or who are immunocompromised due to radio or chemotherapy or from taking certain drugs may have reduced numbers of DCs. In these individuals, it would be desirable to increase the numbers of DCs, including pDCs and cDCs. Thus, there is a need in the art for methods of DC induction, either in vitro or in vivo.

BRIEF SUMMARY OF THE INVENTION

The invention provides induction of DCs from precursor hematopoietic cells by M-CSF. This induction is independent of induction by FL. DCs induced by the methods of the invention are able to regulate immune responses, for example, by producing anti-viral cytokines, such as IFN-I.

The invention is based on the unexpected observation that M-CSF induces BM cultures to produce IFN-α in response to CpG. In fact, these M-CSF-induced BM cells are by phenotype and function similar to pDCs and cDCs and are called pDC and cDC.

The receptors for FL and M-CSF, Flt3 and c-fms respectively, are Group III receptor tyrosine kinases and share structural identity. Induction of DC differentiation by M-CSF, though, does not involve cross-reaction with the FL receptor, as demonstrated by experiments in which either the FL receptor or the M-CSF receptor were inhibited. Furthermore, both pDC and cDC populations developed in M-CSF BM cultures from FL knockout mice (FLKO), ruling out that M-CSF induction of these cells requires an indirect contribution of endogenous FL. Finally, when either wild type or FLKO mice were treated with M-CSF, pDCs and cDCs developed in vivo.

These results indicate that M-CSF can induce the development of pDCs and cDCs. It is possible that in natural, in vivo settings both FL and M-CSF work together to induce and regulate normal DC homeostasis. This is because infections that enhance DCs and immune conditions that result in increases or decreases in DC levels are often associated with increased levels of circulating FL and some of these same conditions have also been reported to enhance circulating M-CSF levels. For example, Langerhans cell histiocytosis demonstrates increased FL and M-CSF in the serum of patients (28), viral infections shown to increase circulating FL also increase M-CSF (29-32), the serum of Systemic Lupus Erythematosus (SLE) patients has increased FL (33), and animal models of SLE demonstrate elevated M-CSF levels (34). However, as shown here, M-CSF can clearly act independently of FL to induce DC development. It is possible that if conditions exist where M-CSF is induced but not FL, or vice versa. Thus, under some conditions DC may be induced that are derived from M-CSF or FL, without the influence of the other growth factor.

The methods of the invention allow for increased levels of pDCs and cDCs after being applied to individuals in vivo. These cells can be used to defend against infections, and mount or direct immune responses. In addition, the invention provides for therapeutic and prophylactic treatments against cancers that do not involve csf-1 mutations, for example, but not limited to, Acute Myelogenous Leukemia (AML, also known as Acute Myelogenous Leukemia) of the type still responsive to M-CSF treatment and including those patients that are receiving therapy for overactive Flt3. The invention also extends to therapeutic and prophylactic treatment against autoimmune diseases, such as SLE.

In an embodiment of the invention, DCs can be produced in vitro by culturing hematopoietic precursor cells in the presence of M-CSF. The hematopoietic precursor cells that can be induced are, but are not limited to, bone marrow cells.

In a further embodiment of the invention, DCs induced by M-CSF in vitro can be used to produce cytokines. These cytokines include, but are not limited to IFN-I, IL-1, IL-6, IL-8, IL-10, IL-12, IL-15, IL-16, IL-18, IL-23, IL-27, IL-28, IL-29, TNF-α, TNF-β and chemokines. The cytokines can be produced either in vitro or in vivo after the M-CSF induced DCs are introduced into an animal. In vivo, the induced DCs stimulate either innate immune responses or adaptive immune responses.

In yet other embodiments of the invention, DCs induced by M-CSF in vitro can be exposed to antigens to stimulate specific immune responses.

In further embodiments of the invention, the DCs generated by M-CSF can be used to stimulate immune responses in other immune cells.

The invention includes a method of increasing dendritic cells (DCs) in vitro, comprising culturing hematopoietic precursor cells; quantitating the number of DCs or eliminating any DCs within the bone marrow; administering Macrophage-Colony Stimulating Factor (M-CSF); quantitating the number of dendritic cells present after administration of M-CSF; wherein the number of DCs after M-CSF administration is increased over the number of DCs before administration of M-CSF. In embodiments of the invention, the precursor cells are bone marrow cells. In other embodiments of the invention, the DCs are plasmacytoid dendritic cells (pDCs) and the number of pDCs is quantitated by measuring the level of at least one cell surface marker, including but not limited to, CD11c, CD45R, CD45RA, PDCA-1, CCR9, Ly49Q, Ly6C, Siglec-H, HLA-DR, CD4, CD123, BDCA-2, BDCA4. In other embodiments of the invention, DCs are conventional dendritic cells (cDCs), which are quantitated by measuring the level of at least one cell surface marker, including but not limited to CD11c, CD11b, CD4, CD8, Sirp-alpha, DEC-205, MHCII, 33D1, HLA-DR, and BDCA-1. In other embodiments of the invention, M-CSF is administered in an MVA vector. In other embodiments of the invention, M-CSF is administered in another viral vector. In yet other embodiments of the invention, the method of increasing DCs further comprises stimulating the DCs by exposing them to a stimulatory agent, wherein the stimulatory agent includes, but is not limited to, a TLR-agonist, virus, bacteria, fungi, plant, or parts thereof, or cytokines including but not limited to IFN-I, IL-10, IL-12, IL-6, and TNF-α. Embodiments of the invention also include a step of reintroducing the harvested dendritic cells into the animal. In yet other embodiments of the invention, the DCs can be pDCs or cDCs or both.

Another embodiment of the invention is a method of increasing dendritic cells in an animal, comprising co-administering M-CSF with an antigen to the animal; wherein the co-administration results in an increase in the number of DCs in the animal. Further embodiments of the invention include antigens that are derived from tumors, viruses, bacteria, fungi, parasites, prions, plants, mollusks, arthropods, or vertebrate toxins. In other embodiments of the invention the animal is a mouse or a human. The invention encompasses DCs that are pDCs or cDCs. In other embodiments of the invention, M-CSF is administered in an MVA vector. In other embodiments of the invention, M-CSF is administered in another viral vector. In yet another embodiments of the invention, M-CSF is administered in a plasmid or via RNA.

Yet another embodiment of the invention is a method of producing dendritic cells, comprising culturing hematopoietic precursor cells; administering M-CSF to the cultured cells; generating dendritic cells; and harvesting the dendritic cells. In embodiments of the invention, the method can further comprise exposing the dendritic cells to an antigen. The invention encompasses antigens including, but not limited to antigens that are derived from tumors, viruses, bacteria, fungi, parasites, prions, plants, mollusks, arthropods, or vertebrate toxins. Embodiments of the invention also include removing the precursor cells from an animal and reintroducing the harvested dendritic cells into the animal. In yet other embodiments of the invention, the DCs can be pDCs or cDCs. The invention also includes embodiments in which the M-CSF is administered to the cultured cells as a polypeptide or as a nucleic acid that is expressed in the cultured cells wherein the nucleic acid is DNA or RNA. The invention also includes methods wherein the M-CSF is administered to the cultured cells in a Modified Vaccinia virus Ankara (MVA) viral vector.

A further embodiment of the invention includes a method of inducing an immune response to one or more antigens in an animal, comprising removing hematopoietic precursor cells from an animal; culturing the precursor cells; administering M-CSF to the cultured cells; generating dendritic cells; exposing the dendritic cells to antigens; harvesting the primed dendritic cells; and reintroducing the primed dendritic cells into the animal. In the invention, the antigens are derived from tumors, viruses, bacteria, fungi, parasites, prions, plants, mollusks, arthropods, or vertebrates, including toxins. Embodiments of the invention also include administering the tumor antigen to the animal. In yet other embodiments of the invention the animal is a human patient suffering from Systemic Lupus Erythematosus (SLE) and the antigens include peptides based on the anti-idiotypic or CDR regions of SLE-associated autoantibodies (45, 46).

Embodiments of the invention also include an animal that is a human patient suffering from Acute Myeloid Leukemia (AML) or ALL undergoing chemotherapy to inhibit Flt3 or c-kit and the antigen could include novel peptides derived from the patients mutated or duplicated Flt3 or c-kit that are not present in the normal form of these receptors (47).

Another embodiment of the invention is a method of producing interferon-α (IFN-α), comprising culturing hematopoietic precursor cells; administering M-CSF to the cultured cells; and collecting the IFN-α.

Yet another embodiment of the invention is a method of treating a patient suffering from AML, comprising administering M-CSF to the patient suffering from AML and increasing the number of DCs in the patient.

A further embodiment of the invention is a method of treating a patient suffering from SLE, comprising administering M-CSF to the patient suffering from SLE and increasing the number of DCs in the patient.

Yet another embodiment of the invention is a method of stimulating an immune response, comprising culturing a hematopoietic precursor cell; administering M-CSF to the cultured cell; generating a DC; and exposing the DC to an immune cell, wherein the immune cell is stimulated to produce an immune response. The immune cells can be T-cells (including, but not limited to regulatory T-cells, suppressor T-cells, or Killer T-cells), T-helper cells (including, but not limited to, regulatory T-cell, suppressor T-cell, or Killer T-cell), B-cells, Natural Killer Cells, or macrophages. Stimulation of an immune response can be achieved in vitro or in vivo. Furthermore, the immune response can be an anti-allergic immune response, an anti-septic immune response, an anti-graft immune response, an anti-tumor immune response, an anti-autoimmune response, a tolerogenic immune response, an anti-pathogen immune response, or a regulatory immune response.

BRIEF DESCRIPTION OF THE DRAWINGS

FIG. 2 depicts M-CSF-induced pDCs and cDCs development from BM cells, even in the absence of FL. (A) C57BL/6 BM cells depleted of B220+ and CD11c+ cells were incubated for 6 days with M-CSF (20 ng/ml) added at day 0 and again at day 3. On day 6 the cells were harvested and stained with antibodies to detect CD11c and CD45RA expression. Cells with the phenotype of pDCs and cDCs populations are shown boxed in the upper panel. The number of cells in each of the pDC and cDC populations are shown in the lower panel and compared to numbers obtained from day 6 FL-generated DCs also using BM cells depleted of B220+ and CD11c+ cells. Data shown are from one experiment representative of three experiments of day 6 FL cultures and more than five experiments of day 6 M-CSF cultures. (B) BM cells from mice lacking FL were similarly depleted of B220+ and CD11c+ cells and incubated for six days with FL or M-CSF (with additional feeding at day 3). The pDC and cDC populations were also evident in these cultures, indicating that M-CSF could drive the generation of cells with pDC and cDC phenotype, independently of FL. Data from FLKO mice from one experiment that is representative of four experiments.

DETAILED DESCRIPTION OF THE PREFERRED EMBODIMENTS

Figure 3:
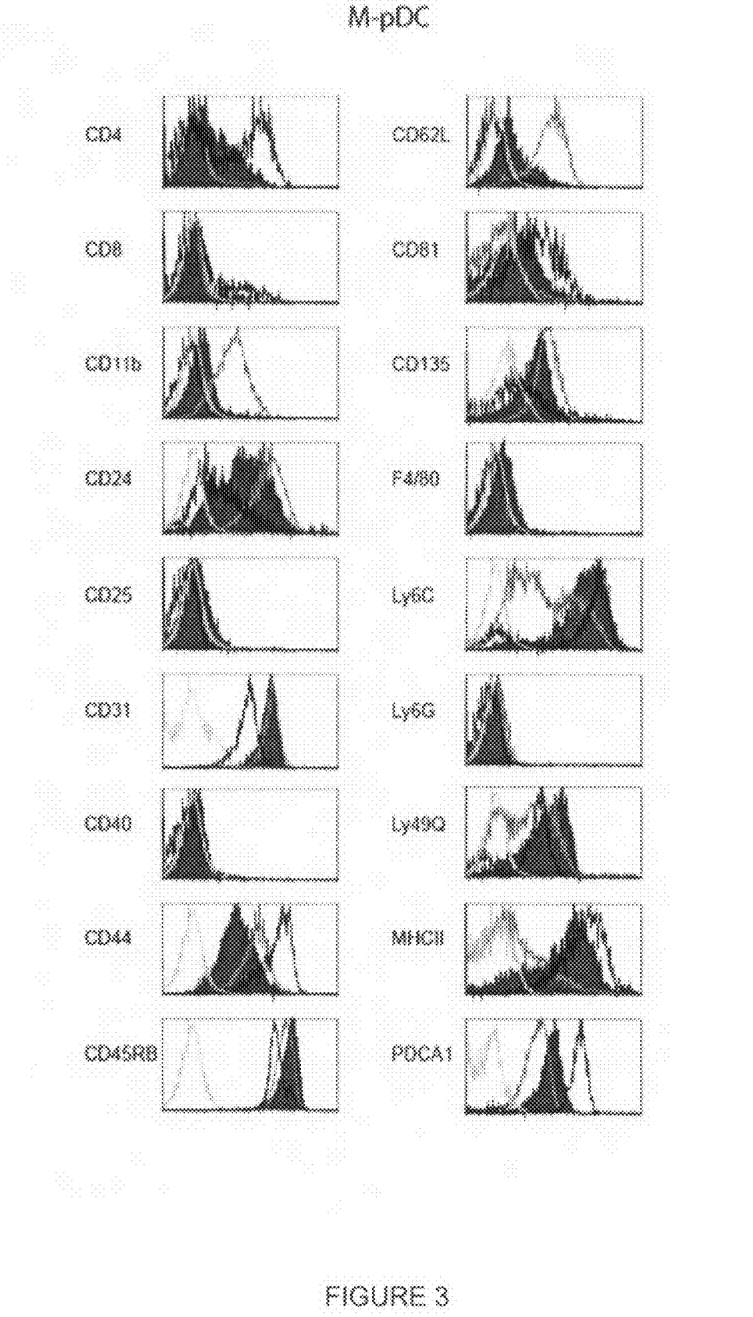
FIG. 3 depicts the surface phenotype of M-CSF-derived pDCs (M-pDCs) compared to FL-derived pDCs (FL-pDCs) and ex-vivo isolated spleen pDC. Stained cells from day 6 M-CSF cultures (filled histograms), FL cultures (grey open histograms), or freshly isolated spleen DCs (black histograms) were gated on pDCs by selecting for the expression of CD11c and CD45RA or CD45R amongst the PI negative cells. The expression of a range of surface markers on the pDC surface is shown. The light grey histograms represent the background staining of the M-pDCs within each stain. All M-pDCs also lacked expression of CD3, CD19, CD49b and NK1.1. The surface phenotypes shown are from one experiment representative of two to five experiments for M-pDC, two to three experiments for FL-pDCs and two experiments for spleen pDCs.
Figure 4:
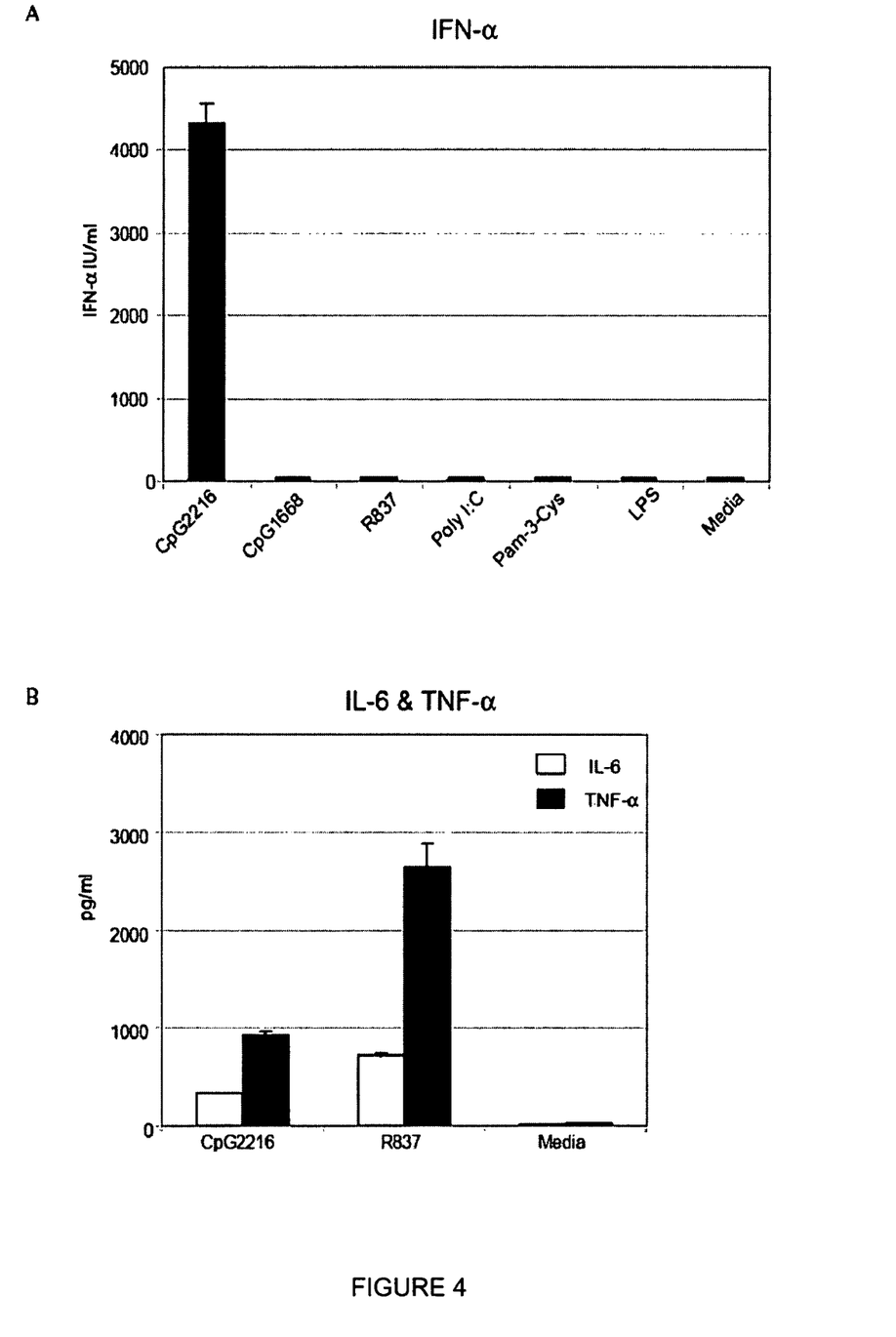
FIG. 4 depicts production of IFN-α by M-pDCs in response to TLR9 stimulation and production of other cytokines in response to TLR7 stimulation. Highly purified, sorted M-pDCs were incubated for 18 hrs with the TLR ligands shown and the supernatants were assayed by ELISA for the presence of IFN-α (A) or by Cytometric Bead Assay (CBA) for the production of IL-6 and TNF-α (B). No IFN-γ, IL-12p70 or MCP-1 were detected by CBA in the M-pDC supernatants. The data shown are from one experiment representative of five experiments (IFN-α ELISA) and three experiments (CBA assay). Error bars represent the range of duplicate samples.
Figure 5:
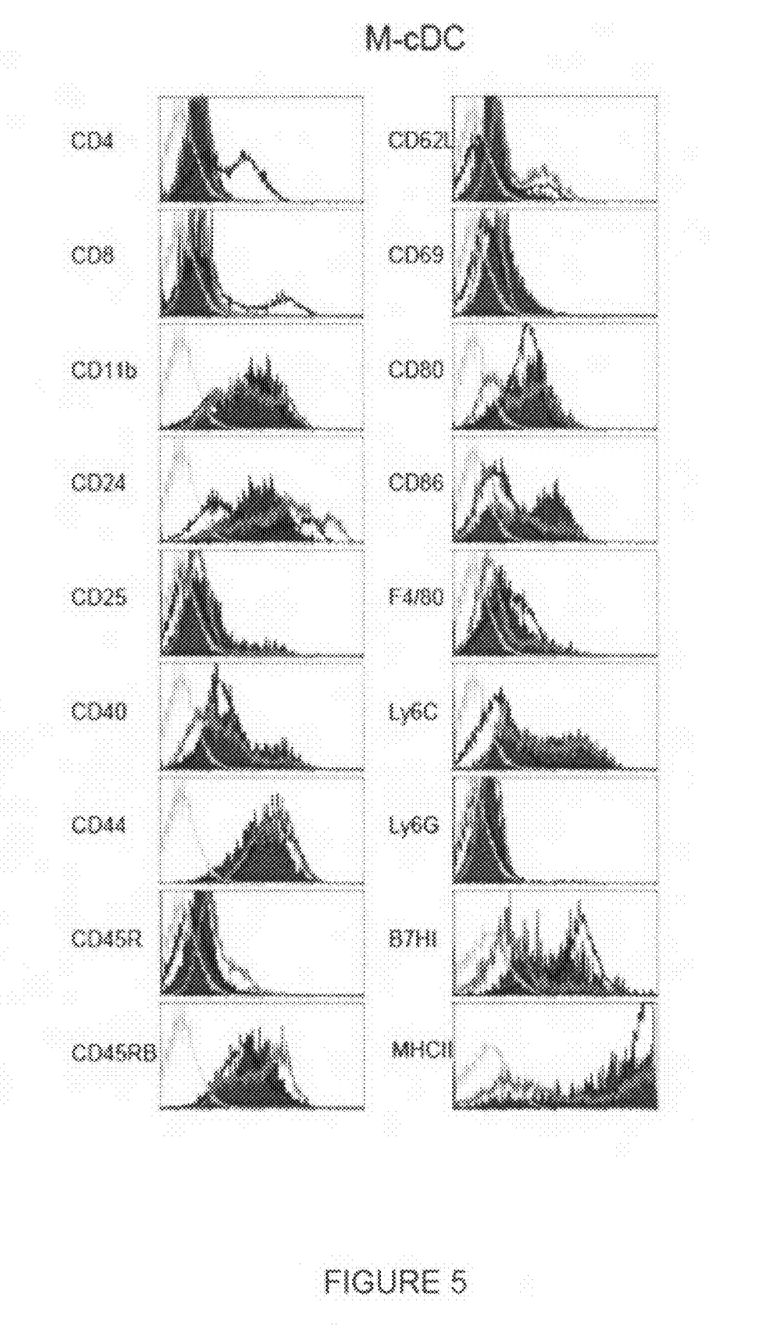
FIG. 5 depicts surface phenotype of M-CSF-derived cDCs (M-cDCs) compared to FL-derived cDCs (FL-cDCs) and ex-vivo isolated spleen cDCs. Stained cells from day 6 M-CSF cultures (filled histograms), FL cultures (grey open histograms) or freshly isolated spleen DCs (black histograms) were gated on cDCs by selecting for the expression of CD11c and lack of CD45RA or CD45R amongst the PI negative cells. The expression of a range of surface markers on the cDC surface is shown. The light grey histograms represent background staining of the M-cDCs within each stain. All M-cDCs also lacked expression of CD3, CD19, CD49b and NK1.1. The surface phenotypes shown are from one experiment representative of two to five experiments for M-cDC, two to three experiments for FL-cDCs and two experiments for spleen cDCs.
Figure 6:
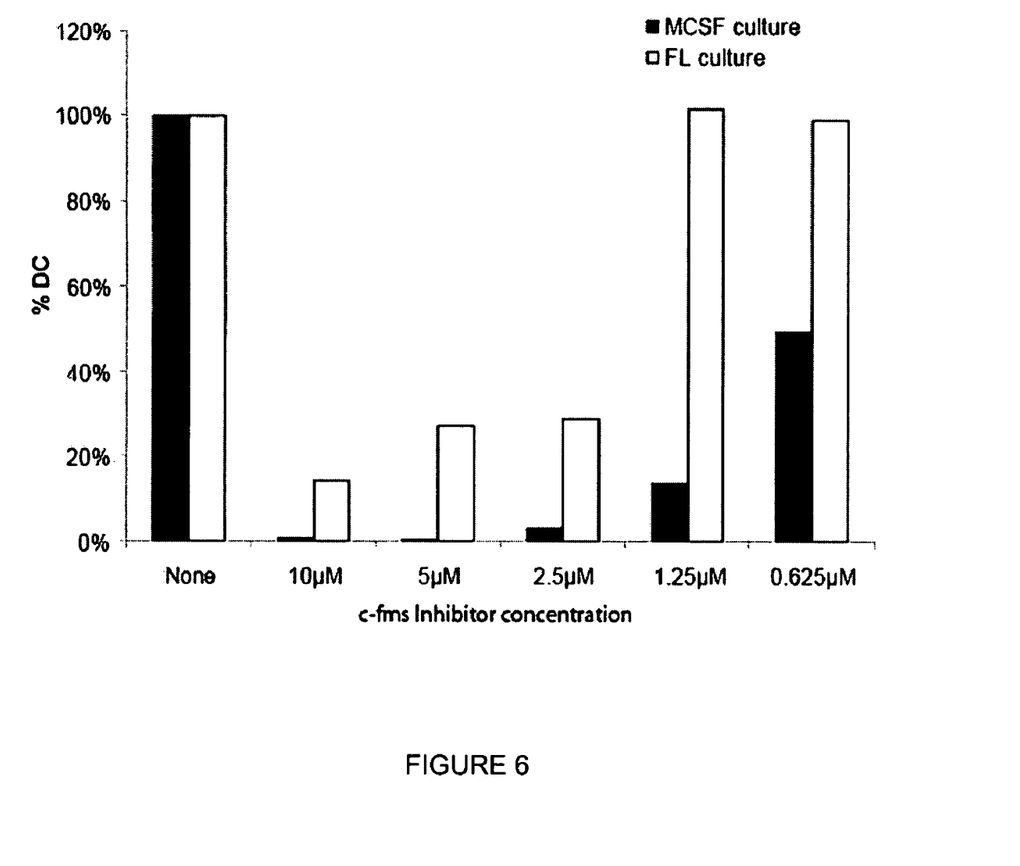
FIG. 6 depicts the inhibition of M-DC development by a c-FMS inhibitor. Replicate M-CSF and FL cultures were conducted in parallel in the presence or absence of a range of cFMS Receptor Tyrosine Kinase Inhibitor concentrations. At the end of the culture period all cells were counted. The number of cells harvested from cultures without inhibitor was set at 100%. Cells from cultures containing inhibitor were expressed as a percentage of cells obtained in the absence of inhibitor. The data shown are from one experiment, representative of two experiments.
Figure 7:
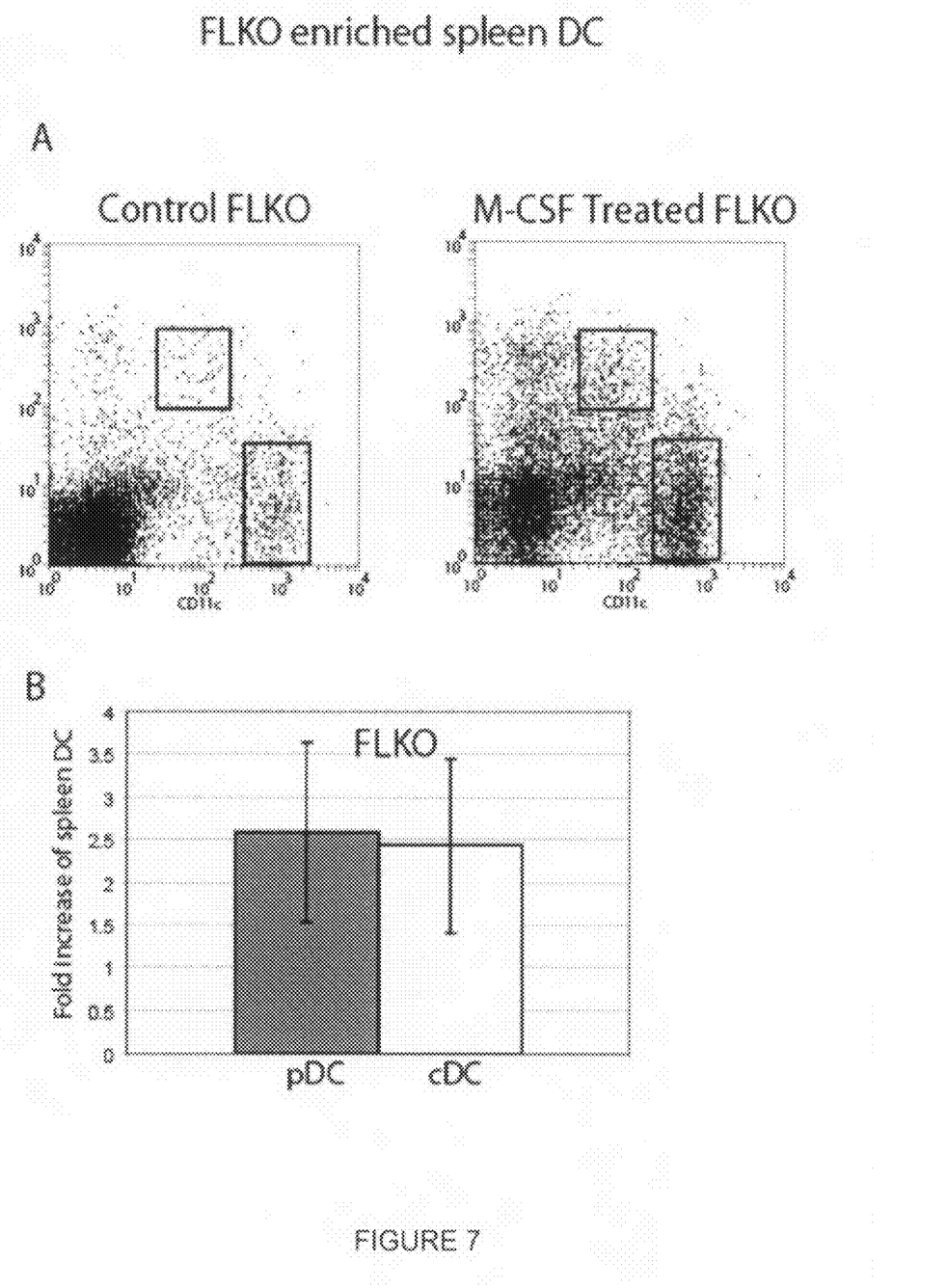
FIG. 7 depicts DC increase due to M-CSF treatment in vivo. FLKO mice were treated for five consecutive days intraperitoneally (ip) with 10 µg/day M-CSF in 0.01% BSA in PBS or with vehicle alone (Control). DCs were purified from FLKO spleens and stained with CD11c and CD45RA. The pDC and cDC populations were gated (A) and enumerated (B). Data are pooled from three individual mice within two separate experiments compared to control mice analyzed the same day.

The invention is supported by experimental results showing that M-CSF induces IFN-α production (FIG. 1) and the development of pDCs and cDCs from hematopoietic precursor cells in vitro (FIG. 2), in the absence of FL. These M-CSF induced pDCs and cDCs are phenotypically identical to pDCs and cDCs induced by FL or those that develop in vivo, (FIGS. 3 and 5) and produce antiviral cytokines, such as IFN-I (FIG. 4). Furthermore, inhibition of the M-CSF receptor, demonstrates that M-CSF inducing activity occurs through its own receptor and not as a cross-reaction with the FL receptor, flt3 (FIG. 6). Finally, M-CSF has been shown to induce pDCs and cDCs in vivo, in an FL-independent pathway (FIG. 7).

In describing the embodiments of the invention the term "induction" refers to the introduction of a signal that results in a change in the morphology and or physiology of a cell. The term "development" refers to the alteration of cell morphology and physiology along a genetically determined pathway. The term "differentiation" refers to the development of a cell from a precursor cell to a more specialized cell type. The term "cell surface marker" refers to a protein or other molecule on the surface of a cell that is specific for that cell, either from any other cell or from other cells in the developmental pathway of the cell. The term "precursor cell" refers to a less differentiated cell that has the ability to develop into a more differentiated cell after induction by some signal. Hematopoietic precursor cells include, but are not limited to, bone marrow cells.

In an embodiment of the invention, DCs are produced in vitro. Hematopoietic precursor cells can be cultured and DCs harvested by techniques known to those of skill in the art, as exemplified, but not limited to, the procedures described in Example 1 below. The number of DCs can be quantitated directly. For example, the number of DCs can be quantitated by measuring DC cell surface antigens, for example, Ly49Q, CD4, MHCII, B7H1, CD81, CD62L, and CD11b, CD45RA, and F4/80, by techniques known to those of skill in the art. These techniques include, but are not limited to, surface staining and fluorescence activated cell sorting (FACS), for example by the methods described in Example 1 below. The number of DCs can also be quantitated indirectly. For example, the number of DCs can be quantitated by measuring DC-specific increases in cytokine production. Quantitation of cytokine production, IFN-I, IFN-α, IL-12 p70, IL-6, TNF-α, MCP-1 and IFN-γ, can be achieved with techniques known to those of skill in the art. These techniques include, but are not limited to, ELISA, as described in Example 1, below. Fold increases in cytokine production can include, but are not limited to, greater than or equal to 1.2 fold, greater than or equal to 1.5 fold, greater than or equal to 2 fold, greater than or equal to 3 fold, greater than or equal to 4 fold, greater than or equal to 5 fold, or greater than or equal to 10 fold.

In embodiments of the invention M-CSF and/or antigen can be administered to cultured cells as a protein. M-CSF protein can be produced by methods known to those of skill in the art, including, but not limited to, in vitro, prokaryotic, and eukaryotic expression systems.

In embodiments of the invention, M-CSF can be administered in vitro to cultured cells at levels including, but not limited to, 1-100 ng/ml, 1-75 ng/ml, 1-50 ng/ml, 1-25 ng/ml, 1-10 ng/ml, 10-100 ng/ml, 10-75 ng/ml, 25-100 ng/ml, 50-100 ng/ml, 75-100 ng/ml, 25-75 ng/ml, or 50-75, ng/ml, preferably at 10-50 ng/ml, and most preferably at 20 ng/ml.

M-CSF and/or antigen can also be administered to cultured cells by introduction of a DNA or RNA that encodes M-CSF and directs its expression within the cultured cell. Techniques for this method of administration include, but are not limited to, techniques for transfection, lipofection, electroporation, and transduction. M-CSF can also be administered to a cell by infection with a virus that carries the genetic information to produce M-CSF. Non-limiting examples of such a virus are DISC-Herpes virus and Modified Vaccinia virus Ankara (MVA). A strain of MVA, MVA-BN is deposited at the European Collection of Animal Cell Cultures (ECACC) with the deposit number V00083008. Those of skill in the art are knowledgeable of these methods of administration. Administration of the M-CSF or antigen to the DC "exposes" the DC to the M-CSF or antigen.

In other embodiments of the invention, antigens can be co-administered to the DCs with M-CSF. These antigens include, but are not limited to, antigens present on viruses (in non-limiting example, influenza, HIV, CMV, EBV, human papilloma virus, adenovirus, HBV, HCV and vaccinia), bacteria, fungi, parasites, prions, and tumor cells (tumor antigens), as well as toxin antigens from viruses, bacteria, fungi, parasites, mollusks, arthropods, and vertebrates. In embodiments of the invention antigens can also include peptides from autoantibodies which can be antigens for the treatment of SLE, and peptides corresponding to the mutant forms of Flt3 or c-kit which can be antigens for the treatment of AML.

The term "co-administration" refers to the administration of more than one substance to an animal or to cultured cells. Co-administration can occur simultaneously or in series, with one substance administered before the other. When administered in series, the second substance can be, but is not limited to, within 1 minute, 2, minutes, 5 minutes, 10 minutes, 30 minutes, 1 hour, 2 hours, 8 hours, 12 hours, 24 hours, 2 days, 3 days, 7 days, 14 days, or 1 month. In embodiments of the invention, DCs generated by administration of M-CSF are also "exposed" to antigen by the co-administration of the antigen.

The term "tumor antigen" refers to an antigen associated with certain tumoral diseases. Tumor antigens are most often antigens encoded by the genome of the host that develops the tumor. Thus, in a strict sense tumor antigens are not foreign antigens. However, tumor antigens are found in significant amounts in tumors; whereas, the amount of tumor antigens in normal tissues is significantly lower, and most often no tumor antigens are found at all in normal tissue. Examples of tumor antigens include gp75 antigen for melanoma papilloma virus proteins for cervical cancer, and tumor specific idiotypic proteins for B cell lymphomas.

In further embodiments of the invention, M-CSF generated DCs are used to stimulate immune responses in other immune cells in vivo or in vitro. These immune cells include, but are not limited to, T-cells (including, but not limited to, regulatory or suppressor T-cells, Killer T-cells (CTLs), and T-Helper cells (including, but not limited to Th1, Th2, and Th17), B cells, Natural Killer cells (NK cells), and macrophages. The stimulated cells can be introduced into an animal in vivo to mount an immune response. Such immune responses include, but are not limited to, anti-allergic responses, anti-septic responses, anti-graft rejection responses, anti-tumor responses, anti-autoimmune disease responses, tolerogenic immune responses, anti-pathogenic immune responses, and regulatory immune responses.

M-CSF generated DCs can also be exposed to stimulatory agents, wherein "stimulatory agents" are proteins and other molecules that induce a specific response from DCs. Stimulatory agents of the invention include, but are not limited to, TLR-agonists, viruses, bacteria, fungi, plants, parasites or parts thereof, or cytokines including but not limited to IFN-I, IL-6, IL-10, IL-12 and TNF-α.

In other embodiments of the invention M-CSF is administered to an animal. The term "animal" includes, but is not limited to vertebrates, most preferably mammals, including, but not limited to humans, horses, cows, pigs, sheep, goats, llamas, cats, dogs, mice, and rats.

In other embodiments of the invention, antigens can be co-administered with M-CSF. There antigens include, but are not limited to, antigens present on viruses (in non-limiting example, influenza, HIV, CMV, EBV, human papilloma virus, adenovirus, HBV, HCV and vaccinia), bacteria, fungi, parasites, prions, and tumor cells (tumor antigens), as well as toxin antigens from viruses, bacteria, fungi, parasites, mollusks, arthropods, and vertebrates. In embodiments of the invention antigens can also include peptides from autoantibodies which can be antigens for the treatment of SLE, and peptides corresponding to the mutant forms of Flt3 or c-kit, which can be antigens for the treatment of AML.

M-CSF and/or antigen can be administered to an animal as a protein, DNA, RNA, or virus. Administration of a protein to an animal can be achieved by, but is not limited to, oral, transdermal, transmucosal administration, or by injection (parenteral). The dose administered can vary depending on which type of administration is used. Pharmaceutically acceptable formulations of M-CSF and antigen are known in the art. Carriers or excipients can be used to produce pharmaceutical compositions. Examples of carriers include, but are not limited to, calcium carbonate, calcium phosphate, various sugars such as lactose, glucose, or sucrose, or types of starch, cellulose derivatives, gelatin, vegetable oils, polyethylene glycols, and physiologically compatible solvents. Examples of physiologically compatible solvents include, but are not limited to sterile solutions of water for injection (WFI), saline solution, and dextrose. M-CSF can be administered by different routes, including but not limited to, intravenous, intraperitoneal, subcutaneous, intramuscular, oral, transmucosal, rectal, or transdermal.

In vivo, M-CSF and/or antigen is administered to an animal at levels of 0.01 μg-100 mg/day, 0.1 μg-100 mg/day, 1 μg-100 mg/day, 10 μg-100 mg/day, 100 μg-100 mg/day, 1 mg-100 mg/day, 10 mg-100 mg/day, 50-100 mg/day, 0.01 μg-10 mg/day, 0.1 μg-10 mg/day, 1 μg-10 mg/day, 10 μg-10 mg/day, 100 μg-10 mg/day, 1-10 mg/day, 10-50 mg/day, 0.01 μg-1 mg/day, 0.1 μg-1 mg/day, 1 μg-1 mg/day, 10 μg-1 mg/day, 100 μg-1 mg/day, 1-10 mg/day, or 1-50 mg/day. Levels of 1-20 μg/day are preferable and 10 μg/day most preferable for administration to rodents. Levels of 1-50 mg/day are preferable, and 25 mg/day most preferable, for humans. M-CSF can also be administered to animals on a per weight basis, including, but not limited to, 0.5 μg-10 g/g weight/day, 1 μg-10 g/g weight/day, 10 μg-10 g/g weight/day, 100 μg-10 g/g weight/day, 1 g-10 g/g weight/day, 0.5 μg-1 g/g weight/day, 1 μg-1 g/g weight/day, 10 μg-1 g/g weight/day, or 100 μg-1 g/g weight/day, preferably 0.5 μg/g weight/day. Other dosages are contemplated by the invention, and can be determined using assays known to the skilled artisan.

Further embodiments of the invention include administration of M-CSF to precursor cells that have been isolated from an animal. These cells are induced by M-CSF in vitro, exposed to antigen, and returned to the animal for a therapeutic or prophylactic effect. Techniques for such "ex vivo" therapies are known to those in the art, as described (36, 37, 44). Other techniques for ex vivo therapy are also contemplated for the invention.

To induce hematopoietic precursor cells in vitro the cells can be cultured and DCs harvested by techniques known to those of skill in the art, as exemplified, but not limited to, the procedures described in Example 1 below. In this embodiment the DCs are characterized by observing DC cell surface antigens, for example CD11c, Ly49Q, CD4, CD8, CD22, DEC-205, 33D1, PDCA-1, BDCA-1, BDCA-2, BDCA-4, CD25, CD80, CD86, CD40, CD69, Siglec-H, Ly6C, CCR9, HLA-DR, CD123, MHCII, B7H1, CD81, CD62L, CD11b, CD45R, CD45RA, and F4/80, by techniques known to those of skill in the art. These techniques include, but are not limited to, surface staining and fluorescence activated cell sorting (FACS), for example by the methods described in Example 1 below. Quantitation of cytokine production can also be used, including, but not limited to, IFN-I, IFN-α, IL-12 p70, IL-6, TNF-α, MCP-1 and IFN-γ. This is achieved with techniques known to those of skill in the art. These techniques include, but are not limited to, ELISA, as described in Example 1, below.

In embodiments of the invention involving ex vivo therapies, M-CSF and/or antigen can be administered to cultured cells as a protein in vitro. M-CSF protein can be produced by methods known to those of skill in the art, including, but not limited to, in vitro, prokaryotic, and eukaryotic expression systems.

In embodiments of the invention, M-CSF and/or antigen is administered in vitro to cultured cells at levels including, but not limited to, 1-100 ng/ml, 1-75 ng/ml, 1-50 ng/ml, 1-25 ng/ml, 1-10 ng/ml, 10-100 ng/ml, 10-75 ng/ml, 25-100 ng/ml, 50-100 ng/ml, 75-100 ng/ml, 25-75 ng/ml, or 50-75, ng/ml, preferably at 10-50 ng/ml, and most preferably at 20 ng/ml.

M-CSF and/or antigen can also be administered to cultured cells by introduction of a DNA or RNA that encodes M-CSF and directs its expression within the cultured cell. Techniques for this method of administration include, but are not limited to, techniques for transfection, lipofection, electroporation, and transduction. M-CSF and/or antigen can also be administered to a cell by infection with a virus that carries the genetic information to produce M-CSF and/or the antigen. Non-limiting examples of such a virus are DISC-Herpes virus and Modified Vaccinia virus Ankara (MVA). A strain of MVA, MVA-BN is deposited at the European Collection of Animal Cell Cultures (ECACC) with the deposit number V00083008. Those of skill in the art are knowledgeable of these methods of administration.

Some autoimmune diseases, for example, but not limited to SLE have been shown to be mediated by the Toll-like receptor 9 (TLR9) (38). TLR9 recognizes DNA and, under certain conditions, can recognize self-DNA in autoimmune disease. In these diseases, B-cells that express TLR9 will proliferate when TLR9 binds to self DNA. In addition, pDCs are also activated by the TLR9-DNA complexes and produce increased levels of IFN-I, which further aggravates the disease. FL induction of pDCs contributes to this aggravation by adding constant stimulation when it induces pDC development. An embodiment of the invention provides a better therapeutic regime, wherein M-CSF is administered to a patient suffering from an autoimmune disease, for example SLE, which acts to prime the new DCs induced by M-CSF. In contrast to treatment with FL, though, not only are DCs induced, but M-CSF also down-regulates TLR9 and its responses to self-DNA complexes (23). Thus, M-CSF-induced DCs can promote specific immune responses in the patient, including but not limited to, down modulation of exaggerated auto-immune reactions, without triggering additional TLR9 IFN-I production and B-cell stimulation.

In another embodiment of the invention, a therapeutic regime for leukemias is provided. These leukemias include, but are not limited to, AML. AML and other leukemias are mediated by activation of Flt3, the receptor for FL (39, 48-50). Thus, in this embodiment of the invention, administration of FL to a patient to induce development of DCs would aggravate the disease. In contrast, the invention provides for administration of M-CSF, along with a tumor antigen, to a patient with leukemia, including, but not limited to AML, so that DCs can be induced to provide an immune response against the tumor cells, without further stimulation of the tumor cells with FL. An inhibitor of Ftl3 can also be used together with M-CSF to treat the leukemias.

Embodiments of the invention are also directed to the treatment of other proliferative disorders including, but not limited to, hematopoietic neoplastic disorders involving hyperplastic/neoplastic cells of hematopoietic origin arising from myeloid, lymphoid or erythroid lineages, or precursor cells thereof. These include, but are not limited to erythroblastic leukemia, acute promyeloid leukemia (APML), chronic myelogenous leukemia (CML), lymphoid malignancies, including, but not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

In addition, embodiments of the invention include, but are not limited to, the treatment of malignancies of epithelial or endocrine tissues, including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include, but are not limited to, those forming from tissue of the cervix, lung, prostate, breast, head and neck, colon and ovary.

This invention will be described in greater detail in the following Examples.

Example 1

Materials and Methods

Mice—C57BL/6 mice were obtained from Harlan Winkelmann (Borchen, Germany) and used at 6-10 weeks of age. FLKO mice were developed as described (14) and bred at the Institute of Labortierkunde (University of Zurich).

Antibodies and Reagents—Recombinant (rec) flag-tagged murine (mu) FL was expressed in CHO cells and purified in house as previously described (10). recmuM-CSF and rechuM-CSF were obtained from Tebu-Bio (Frankfurt, Germany) and rechuM-CSF from R&D Systems (Wiesbaden, Germany). The cFMS Receptor Tyrosine Kinase Inhibitor (Cat. No. 344036) was obtained from EMD Biosciences (Darmstadt, Germany). Oligonucleotides containing CpG motifs (CpG2216 and CpG1668) were synthesized by TIB MOLBIOL (Berlin, Germany) according to published sequences (35). Imiquimod (R837) and palmitoyl-3-cysteine-serine-lysine-4 (Pam-3-Cys) were purchased from InvivoGen (San Diego, USA). Poly(cytidylic-inosinic) acid (poly I:C)), lipopolysaccharide (LPS) and 7-Allyl-7,8-dihydro-8-oxoguanosine (Loxoribine) were purchased from Sigma-Aldrich (Taufkirchen, Germany). All antibodies, unless otherwise stated, were obtained from Becton Dickinson, Germany, with the following exceptions: purified and FITC-conjugated anti-CD11c (rat clone 223H7) and anti-Ly49Q (Biozol Diagnostica Vertrieb GmbH, Eching, Germany), anti-mPDCA-1 (Miltenyi Biotec, Bergisch Gladbach, Germany) and anti-F4/80 (NatuTec GmbH, Frankfurt, Germany). Hybridomas, the supernatants of which were used in the depletion cocktail for ex vivo DC purification (21), were provided by Professor Ken Shortman, WEHI, Melbourne, Australia.

M-CSF and FL BM cultures—BM cells were flushed from femurs and tibiae of mice. Red cell lysis buffer (Sigma-Aldrich) was used to deplete red blood cells from the BM cell suspensions. BM cells were then either cultured directly or after depletion. To deplete, BM cells were incubated for 30 min with rat antibodies to CD11c and CD45R (B220) followed by 30 min incubation with goat anti-rat magnetic beads (Qiagen, Hilden, Germany). The depletion procedure routinely removed 65-80% of total BM cells. It should be noted that depletion with the beads only, in the absence of the rat antibodies, also depleted about 50% of the BM cells, presumably via FcR/Ig interactions. Total BM cells or depleted BM cells were cultured at $1.5 \times 10^6$ cells/ml in RPMI-1640 media (Gibco) supplemented with 10% FCS, 50 μM beta-mercaptoethanol, 100 IU/ml penicillin/streptomycin (complete media) and either 20 ng/ml recmuM-CSF or rechu-MCSF or 35 ng/ml recmuFL for 6-8 days at 37° C. in a humidified atmosphere containing 5% $CO_2$. The M-CSF cultures were fed with fresh M-CSF every 3 days, without media change.

Surface staining of M-CSF or FL BM cultures—Harvested cells were washed in PBS containing 2% FCS and 2 mM EDTA (FACS buffer). FcR binding was then blocked by incubation with 1 mg/ml purified anti CD16/32 monoclonal antibody (clone 2.4G2) for 20 mins on ice. An equal volume of 2× concentrated specific antibody stain was then added to the cell suspension and incubated for a further 20 mins. Cells were washed in FACS buffer and resuspended in FACS buffer containing 1 μg/ml propidium iodide.

Activation of DC subsets and analysis of cytokine production by ELISA—Unsorted M-CSF or FL BM cultures or sorted DCs ($0.25$-$0.5 \times 10^6$ cells/ml) were stimulated for 18-24 hrs in complete media with or without an added stimulus. The stimuli used were as follows: 1 μg/ml Pam-3-Cys, 100 μg/ml poly(I:C), 1 μg/ml LPS, 1 μg/ml R837, 1 mM Loxoribine, 0.5 μM CpG2216, 0.5 μM CpG1668. Culture supernatants were assayed for the presence of IFN-α by two-site ELISA as previously described (21). Other cytokines (IL-12 p70, IL-6, TNF-α, MCP-1 and IFN-γ) were measured using the Cytometric Bead Array, Mouse Inflammation Kit (Becton Dickinson). Stimulated DCs were blocked as stated above and stained with antibodies directed to CD8a, CD40, CD69, CD80 and CD86.

In vivo M-CSF treatment—Wild type and FLKO mice were treated ip with 10 μg of M-CSF in 0.01% BSA (100 μl volume), or with vehicle alone, for five consecutive days. At the end of five days mice were sacrificed. The peritoneum was flushed 3 times with Complete media and then organs were collected for DC purification.

Ex vivo DC purification—DCs were purified from spleens of M-CSF or vehicle treated mice essentially as previously described (21), using FACS buffer, RPMI and 1.077A Nycodenz (Progen Biotechnik GmbH, Heidelberg, Germany) that was adjusted to mouse osmolarity (308 mOsm).

Example 2

Figure 1:
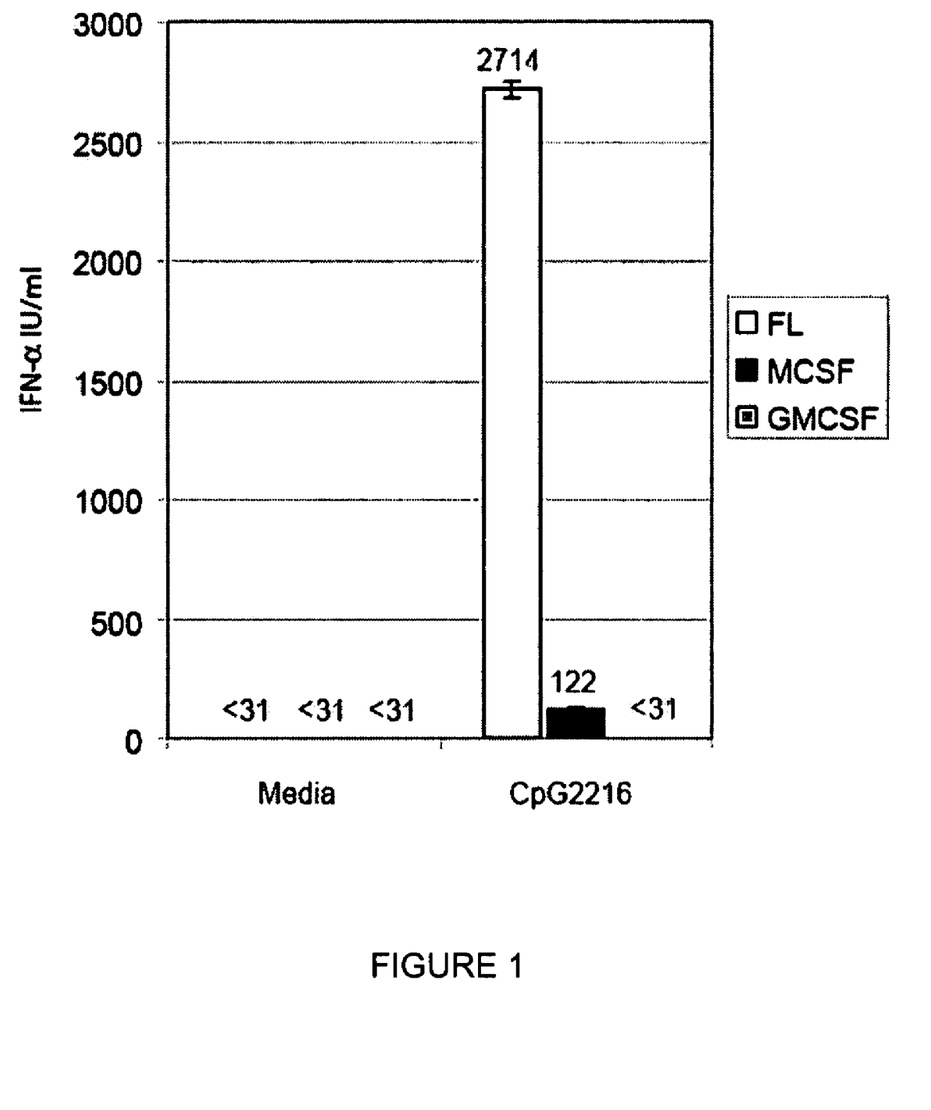
FIG. 1 depicts that M-CSF- and FL-derived BM, but not GM-CSF derived BM, promote IFN-α production to CpG2216. BM cells were incubated for six days with FL (35 ng/ml), GM-CSF (50 ng/ml), or M-CSF (50 ng/ml). M-CSF and GM-CSF were added at day 0 and again at day 5. On day 6 CpG2216 (500 nM) was added to the total cultures or left without stimulation (media) for another day. Cell culture supernatant was analyzed for IFN-α content by ELISA.

Total BM Cells Cultured with M-CSF are Potent Producers of IFN-α in Response to CpG-ODN Culture of mouse bone marrow (BM) cells with FL for 8-10 days has been reported to lead to the generation of millions of highly pure pDCs and cDCs that closely resemble the DC populations of steady state mouse spleen (19). To routinely test the kinetics of pDC development within these FL cultures, the IFN-α producing capacity of total BM cells incubated with FL in a multiwell format over a time course of 0-7 days was analyzed. A parallel culture of total BM cells with M-CSF was included as a negative control, because M-CSF is routinely used to generate macrophages from BM cells. Usually, the media and M-CSF are replaced every few days and only adherent cells are harvested at the end of a culture period of 7 days or longer (17). Instead, M-CSF cultures were treated exactly as the FL cultures, and wells of total M-CSF cultures (including adherent and non-adherent cells) were analyzed for IFN-α production in response to CpG-2216. Unexpectedly, IFN-α was induced to high levels in the M-CSF cultures (FIG. 1). Moreover, the IFN-α produced in response to CpG- 2216 increased with culture time, implying that IFN-α producing cells were being generated in the course of the M-CSF culture.

Example 3

The IFN-α Producers Induced in M-CSF BM Cultures Display Characteristics of pDC, but Develop without the Influence of FL Depletion of pDCs and cDCs from total BM cells depleted the CpG-induced IFN-α producing capacity of BM cells. When the DC-depleted BM cells were cultured with M-CSF for 6 days, potent IFN-α producing capacity was detected again in the non-adherent cells of the M-CSF culture.

Figure 2:
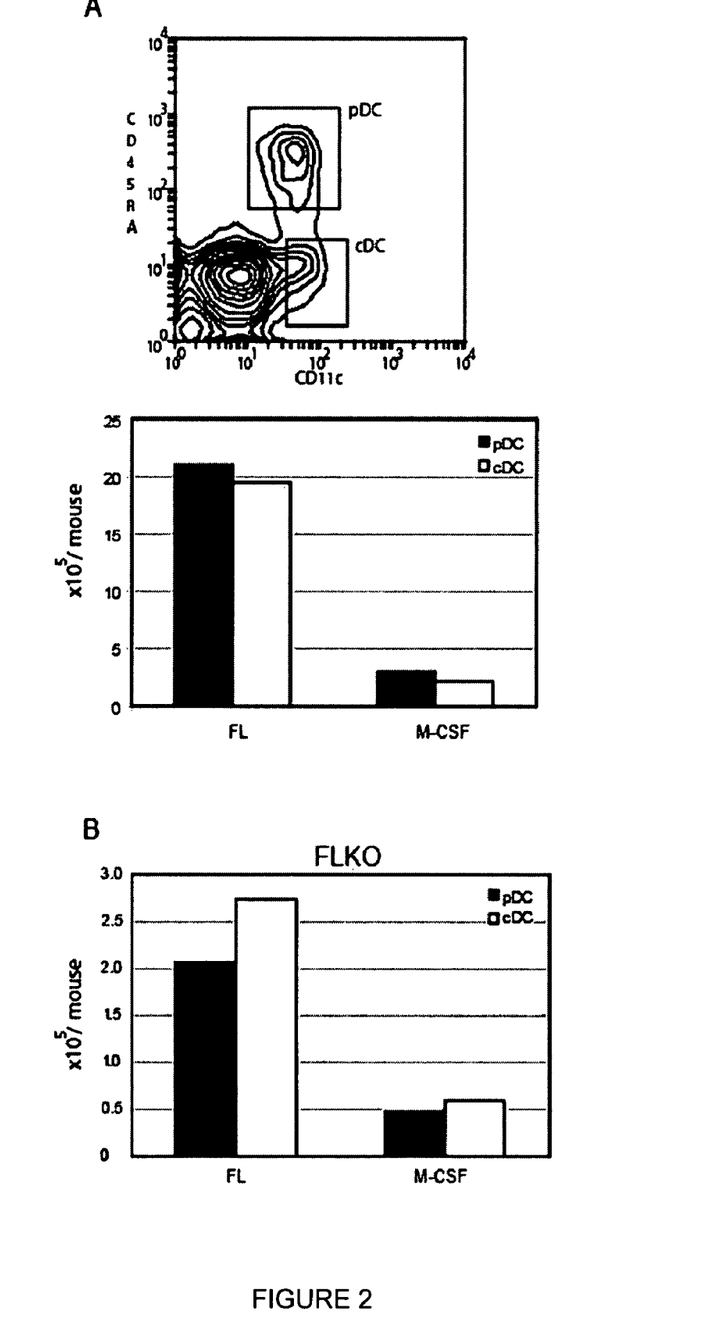

To determine whether any of the non-adherent M-CSF-generated cells displayed the phenotype expected of a pDCs they were stained with CD11c and CD45RA. Indeed, a population of 10-20% of cells within the cultures expressed high levels of CD45RA and medium levels of CD11c, together with the lack of CD3, CD19 or CD49b or NK1.1 expression, low side scatter and forward scatter this was commensurate with the phenotype of pDCs (FIG. 2a).

It was clear that M-CSF could drive pDC development yet the yield of pDCs was substantially less then that obtained with FL. When the two cultures were compared side by side after six days of culture, M-CSF was approximately 10-fold less efficient than FL. Day 6 was chosen for comparison because after this stage the M-CSF cultures become very acidic and sorted DC populations from the cultures died much more rapidly in culture and failed to produce cytokines.

To determine if M-CSF induction of pDCs requires endogenous FL, replicate BM cultures were studied from mice in which the FL gene had been ablated (FLKO mice). Total cell numbers obtained from the BM cultures of FLKO mice were reduced whether cultures were conducted with M-CSF addition or FL addition (FIG. 1b), indicating that pDCs developed even in the absence of FL. It was clear that cells with the phenotype and morphology of pDCs were produced by culture of BM first depleted of any DC populations and in the presence of only exogenous M-CSF, without the potential influence of any FL. These M-CSF generated pDCs are referred to as M-pDC.

Example 4

Detailed Surface Phenotype of M-pDC

Extensive phenotyping of the M-pDCs from wild type and FLKO mice shows that the elicited pDCs displayed, an identical phenotype for over 40 surface markers. When compared to pDCs generated in vitro with FL (FL-pDC), numerous cell surface markers were different between the pDCs generated with the two different cytokines. In fact, as seen in FIG. 3, the M-pDCs displayed a phenotype that appeared for many markers to be intermediate between FL-pDC and ex-vivo isolated spleen pDC. Molecules that are recognized as differentiation markers of pDC; Ly49Q (20), CD4 (21) and MHCII, are all higher on M-pDCs than on FL-pDCs and are very similar to the levels on spleen pDCs. The M-pDCs express a similarly high level of Ly6C as the ex vivo spleen pDCs. Because it has recently been shown that pDC develop from Ly6C⁻ precursors, M-pDCs represent a further differentiated state in pDC development than the FL-pDC (22).

The surface expression of B7H1, CD81, CD62L and CD11b on the M-pDCs also more closely resemble the ex-vivo pDCs than the FL-pDC.s. In contrast, M-pDCs express the lowest levels of CD44 and a spread of surface CD24 bridging the high levels expressed by spleen pDCs and the low levels expressed by FL-pDCs. Also, M-pDCs express low levels of F4/80. The low F4/80 expression lends a "myeloid" phenotype to the M-pDCs. M-pDCs express very low levels of CD11b (in the order of 10-fold lower than FL-pDC) and do not express Ly6G.

Example 5

Highly Purified M-pDCs are Activated by Ligands for TLR7 and TLR9

Similar to FL-pDCs and ex-vivo pDCs, sorted M-pDC were activated with ligands for TLR7 and 9. In response to a type A CpG-ODN (CpG2216) M-pDCs produced high levels of IFN-α. In response to the TLR7 ligand R837 the M-pDCs produced low but substantial levels of IFN-α (FIG. 4A). Other cytokines induced by these TLR ligands included IL-6 and TNF-α (FIG. 4B), with highest levels induced by R837.

After overnight stimulation the M-pDCs were examined for changes in phenotype. The M-pDCs, similarly to FL-pDCs and ex-vivo pDCs, expressed elevated levels of CD8a, CD69, CD86 and CD40 upon TLR stimulation.

Example 6

Conventional DCs also Develop in M-CSF BM Cultures

As shown in FIG. 1, CD11c⁺ cells that did not concomitantly express CD45RA or T, B or NK cell markers were also induced in the M-CSF BM cultures. Like the pDCs, these cells also developed in BM cultures of FLKO mice. Surface phenotype analyses of these cells reveals that they resemble conventional (c) DC, expressing costimulation markers and MHCII (FIG. 5). These cDCs were of quite a mature phenotype, with higher levels of surface MHCII and co-stimulation markers than the cDCs induced in FL cultures. Upon TLR stimulation the cDC were activated to resemble mature, ex-vivo activated cDCs.

Of interest in the activation of the M-cDCs and M-pDCs is that they respond well to TLR9 ligands. This is quite a different scenario from macrophages within M-CSF cultures that downregulate TLR9 and consequently respond poorly to TLR9 ligands (23).

Example 7

M-pDC Generation is Dependent Upon Active c-fms

It has previously been shown that Flt3+ cells within the BM common myeloid progenitors (CMP) and common lymphoid progenitors (CLP) are the precursors of cDCs and pDCs within mouse lymphoid organs (24,25) and it has been assumed that FL is essential for DC development. Thus the generation of DCs, particularly the generation of pDCs with a typical monocytic protein, in the absence of FL, was unexpected. As shown in FIG. 1 the M-pDCs clearly develop in the absence of FL, yet they also show many similarities to FL-pDCs. Given that M-CSF and FL, as well as their respective receptors, Flt3 and c-fms, have structural similarities, whether M-CSF was signalling through Flt3 was investigated. That is, whether M-CSF would act as a FL surrogate that also signalled via Flt3, generating M-CSF-induced "FL-DCs" was examined.

There are numerous inhibitors of receptor tyrosine kinases, with varying levels of cross-reactivity. The inhibitor cFMS Receptor Tyrosine Kinase Inhibitor (Calbiochem), which is reported to be a highly specific c-fms inhibitor, was used. Indeed, cFMS Receptor Tyrosine Kinase Inhibitor entirely blocked the haematopoietic effects of M-CSF over a broad concentration range (FIG. 6). The highest concentrations of inhibitor also blocked the generation of DCs by FL. However, cFMS inhibitor used in the range of 0.63-1.3 μM had only minor effects on FL-mediated FL-DC generation (FIG. 6). Since these same low concentrations still blocked M-DC generation, M-pDC generation does not involve M-CSF acting through the Flt3 receptor tyrosine kinase. Although the c-fms inhibitor is likely a promiscuous receptor tyrosine kinase inhibitor at high concentrations, at low concentrations it did not inhibit FL-DC generation, demonstrating that it is, indeed, c-fms specific. Thus, M-pDCs and M-cDCs can be generated by M-CSF via c-FMS signalling, independently of Flt3 and FL in vitro.

Example 8

Administration of M-CSF in Vivo

The FLKO mice display a major defect in pDC and cDC numbers. In the spleen they have only about 12% of the DC numbers of wild type C57BL/6 mice. These mice also have reduced CFU-GM cells within BM (14). As FL acts upon early hematopoietic stem cells, as well as later stage DC precursors, it is possible that the major reduction of DCs within these mice is a due to a combination of a lack of DCs that require FL for later development and of DCs that require FL for early precursor development, but are independent of FL once committed to the DC lineage. On the other hand, it has recently been reported that op/op mice that carry a mutation in the gene for M-CSF and thus lack functional M-CSF, exhibit reduced numbers of splenic DC (26). Specifically, cDCs were reduced about 2-fold and pDCs about 3-fold. This was substantially less of an effect than that seen in mice lacking FL, but nevertheless, the lack of M-CSF did result in reduced cell DC numbers, a result consistent with the in vitro data.

Whether exogenously applied M-CSF increases DC numbers in mice was tested. Previously, exogenous M-CSF concentrations in the range of 10 to 200 μg/day. The source and specific activity of M-CSF used has varied widely and consequently and it has been reported that M-CSF has an extremely short half-life of only 10 mins in circulation (27). Here, M-CSF was administered at 10 μg/day of m-CSF to C57BL/6 or FLKO mice for 5 days. After the 5 day application period a huge increase in F4/80$^{hi}$ cells was observed in peritoneal lavages of the one treated wild type and treated FLKO mice that we examined. These observations indicate that indeed M-CSF was inducing an effect in vivo. Analysis of DC populations in the spleen revealed that M-CSF was inducing a reproducible increase of about 2-fold in both pDC and cDC numbers. This increase was evident in both the single C57BL/6 and all 3 FLKO mice (FIG. 7). A more extensive DC increase (greater than 6-fold) was evident in the peritoneal lavage of the C57BL/6 mouse examined.

REFERENCES

The following references are cited herein. The entire disclosure of each reference is relied upon and incorporated by reference herein.

1. Steinman, R. M. and K. Inaba. 1999. Myeloid dendritic cells. *J Leukoc. Biol.* 66:205-208.
2. Shortman, K. and Y. J. Liu. 2002. Mouse and human dendritic cell subtypes. *Nat. Rev. Immunol.* 2:151-161.
3. Scheicher, C., M. Mehlig, R. Zecher, and K. Reske. 1992. Dendritic cells from mouse bone marrow: in vitro differentiation using low doses of recombinant granulocyte-macrophage colony-stimulating factor. *J Immunol Methods* 154:253-264.
4. Inaba, K., M. Inaba, N. Romani, H. Aya, M. Deguchi, S. Ikehara, S. Muramatsu, and R. M. Steinman. 1992. Generation of large numbers of dendritic cells from mouse bone marrow cultures supplemented with granulocyte/macrophage colony-stimulating factor. *J Exp. Med.* 176:1693-1702.
5. Sallusto, F. and A. Lanzavecchia. 1994. Efficient presentation of soluble antigen by cultured human dendritic cells is maintained by granulocyte/macrophage colony-stimulating factor plus interleukin 4 and downregulated by tumor necrosis factor alpha. *J Exp. Med.* 179:1109-1118.
6. Vremec, D., G. J. Lieschke, A. R. Dunn, L. Robb, D. Metcalf, and K. Shortman. 1997. The influence of granulocyte/macrophage colony-stimulating factor on dendritic cell levels in mouse lymphoid organs. *Eur. J. Immunol.* 27:40-44.
7. Gilliet, M., A. Boonstra, C. Paturel, S. Antonenko, X. L. Xu, G. Trinchieri, A. O'Garra, and Y. J. Liu. 2002. The development of murine plasmacytoid dendritic cell precursors is differentially regulated by FLT3-ligand and granulocyte/macrophage colony-stimulating factor. *J. Exp. Med* 195:953-958.
8. Brasel, K., S. T. De, J. L. Smith, and C. R. Maliszewski. 2000. Generation of murine dendritic cells from flt3-ligand-supplemented bone marrow cultures. *Blood* 96:3029-3039.
9. Brawand, P., D. R. Fitzpatrick, B. W. Greenfield, K. Brasel, C. R. Maliszewski, and T. De Smedt. 2002. Murine plasmacytoid pre-dendritic cells generated from Flt3 ligand-supplemented bone marrow cultures are immature APCs. *J. Immunol.* 169:6711-6719.
10. O'Keeffe, M., H. Hochrein, D. Vremec, J. Pooley, R. Evans, S. Woulfe, and K. Shortman. 2002. Effects of administration of progenipoietin 1, Flt-3 ligand, granulocyte colony-stimulating factor, and pegylated granulocyte-macrophage colony-stimulating factor on dendritic cell subsets in mice. *Blood* 99:2122-2130.
11. Pulendran, B., J. Banchereau, S. Burkeholder, E. Kraus, E. Guinet, C. Chalouni, D. Caron, C. Maliszewski, J. Davoust, J. Fay, and K. Palucka. 2000. Flt3-ligand and granulocyte colony-stimulating factor mobilize distinct human dendritic cell subsets in vivo. *J. Immunol.* 165:566-572.
12. Maraskovsky, E., K. Brasel, M. Teepe, E. R. Roux, S. D. Lyman, K. Shortman, and H. J. McKenna. 1996. Dramatic increase in the numbers of functionally mature dendritic cells in Flt3 ligand-treated mice: multiple dendritic cell subpopulations identified. *J. Exp. Med* 184:1953-1962.
13. Bjorck, P. 2001. Isolation and characterization of plasmacytoid dendritic cells from Flt3 ligand and granulocyte-macrophage colony-stimulating factor-treated mice. *Blood* 98:3520-3526.
14. McKenna, H. J., K. L. Stocking, R. E. Miller, K. Brasel, S. T. De, E. Maraskovsky, C. R. Maliszewski, D. H. Lynch, J. Smith, B. Pulendran, E. R. Roux, M. Teepe, S. D. Lyman, and J. J. Peschon. 2000. Mice lacking flt3 ligand have deficient hematopoiesis affecting hematopoietic progenitor cells, dendritic cells, and natural killer cells. *Blood* 95:3489-3497.

15. Ishii, K. J. and S. Akira. 2006. Innate immune recognition of, and regulation by, DNA. *Trends Immunol* 27:525-532.
16. Diebold, S. S., M. Montoya, H. Unger, L. Alexopoulou, P. Roy, L. E. Haswell, A. Al Shamkhani, R. Flavell, P. Borrow, and Reis e Sousa. 2003. Viral infection switches non-plasmacytoid dendritic cells into high interferon producers. *Nature* 424:324-328.
17. Hochrein, H., B. Schlatter, M. O'Keeffe, C. Wagner, F. Schmitz, M. Schiemann, S. Bauer, M. Suter, and H. Wagner. 2004. Herpes simplex virus type-1 induces IFN-alpha production via Toll-like receptor 9-dependent and -independent pathways. *Proc. Natl. Acad. Sci. U.S.A* 101: 11416-11421.
18. Krug, A., S. Rothenfusser, V. Hornung, B. Jahrsdorfer, S. Blackwell, Z. K. Ballas, S. Endres, A. M. Krieg, and G. Hartmann. 2001. Identification of CpG oligonucleotide sequences with high induction of IFN-alpha/beta in plasmacytoid dendritic cells. *Eur. J. Immunol.* 31:2154-2163.
19. Naik, S. H., A. I. Proietto, N. S. Wilson, A. Dakic, P. Schnorrer, M. Fuchsberger, M. H. Lahoud, M. O'Keeffe, Q. X. Shao, W. F. Chen, J. A. Villadangos, K. Shortman, and L. Wu. 2005. Cutting edge: generation of splenic CD8+ and CD8− dendritic cell equivalents in Fms-like tyrosine kinase 3 ligand bone marrow cultures. *J. Immunol.* 174:6592-6597.
20. Omatsu, Y., T. Iyoda, Y. Kimura, A. Maki, M. Ishimori, N. Toyama-Sorimachi, and K. Inaba. 2005. Development of Murine Plasmacytoid Dendritic Cells Defined by Increased Expression of an Inhibitory NK Receptor, Ly49Q. *J Immunol* 174:6657-6662.
21. O'Keeffe, M., H. Hochrein, D. Vremec, I. Caminschi, J. L. Miller, E. M. Anders, L. Wu, M. H. Lahoud, S. Henri, B. Scott, P. Hertzog, L. Tatarczuch, and K. Shortman. 2002. Mouse plasmacytoid cells: long-lived cells, heterogeneous in surface phenotype and function, that differentiate into CD8(+) dendritic cells only after microbial stimulus. *J. Exp. Med* 196:1307-1319.
22. Kreisel, F. H., A. Blasius, D. Kreisel, M. Colonna, and M. Cella. 2006. Interferon-producing cells develop from murine CD31(high)/Ly6C(−) marrow progenitors. *Cell Immunol* 242:91-98.
23. Sweet, M. J., C. C. Campbell, D. P. Sester, D. Xu, R. C. McDonald, K. J. Stacey, D. A. Hume, and F. Y. Liew. 2002. Colony-stimulating factor-1 suppresses responses to CpG DNA and expression of toll-like receptor 9 but enhances responses to lipopolysaccharide in murine macrophages. *J Immunol* 168:392-399.
24. D'Amico, A. and L. Wu. 2003. The early progenitors of mouse dendritic cells and plasmacytoid predendritic cells are within the bone marrow hemopoietic precursors expressing Flt3. *J. Exp. Med* 198:293-303.
25. Karsunky, H., M. Merad, A. Cozzio, I. L. Weissman, and M. G. Manz. 2003. Flt3 ligand regulates dendritic cell development from Flt3+ lymphoid and myeloid-committed progenitors to Flt3+ dendritic cells in vivo. *J Exp. Med.* 198:305-313.
26. MacDonald, K. P., V. Rowe, A. D. Clouston, J. K. Welply, R. D. Kuns, J. L. Ferrara, R. Thomas, and G. R. Hill. 2005. Cytokine expanded myeloid precursors function as regulatory antigen-presenting cells and promote tolerance through IL-10-producing regulatory T cells. *J. Immunol.* 174:1841-1850.
27. Bartocci, A., D. S. Mastrogiannis, G. Migliorati, R. J. Stockert, A. W. Wolkoff, and E. R. Stanley. 1987. Macrophages specifically regulate the concentration of their own growth factor in the circulation. *Proc. Natl. Acad. Sci. U.S.A* 84:6179-6183.
28. Rolland, A., L. Guyon, M. Gill, Y. H. Cai, J. Banchereau, K. McClain, and A. K. Palucka. 2005. Increased blood myeloid dendritic cells and dendritic cell-proteins in Langerhans cell histiocytosis. *J Immunol* 174:3067-3071.
29. Guha-Thakurta, N. and J. A. Majde. 1997. Early induction of proinflammatory cytokine and type I interferon mRNAs following Newcastle disease virus, poly [rl:rC], or low-dose LPS challenge of the mouse 1. *J Interferon Cytokine Res.* 17:197-204.
30. Vollstedt, S., M. O'Keeffe, B. Ryf, B. Glanzmann, H. Hochrein, and M. Suter. 2006. The long-term but not the short-term antiviral effect of IFN-alpha depends on Flt3 ligand and pDC. *Eur. J. Immunol.* 36:1231-1240.
31. Franchini, M., H. Hefti, S. Vollstedt, B. Glanzmann, M. Riesen, M. Ackermann, P. Chaplin, K. Shortman, and M. Suter. 2004. Dendritic cells from mice neonatally vaccinated with modified vaccinia virus Ankara transfer resistance against herpes simplex virus type I to naive one-week-old mice. *J. Immunol.* 172:6304-6312.
32. Itoh, Y., T. Okanoue, S. Sakamoto, K. Nishioji, and K. Kashima. 1997. The effects of prednisolone and interferons on serum macrophage colony stimulating factor concentrations in chronic hepatitis B. *J Hepatol.* 26:244-252.
33. Gill, M. A., P. Blanco, E. Arce, V. Pascual, J. Banchereau, and A. K. Palucka. 2002. Blood dendritic cells and DC-proteins in systemic lupus erythematosus. *Hum. Immunol.* 63:1172-1180.
34. Chitu, V. and E. R. Stanley. 2006. Colony-stimulating factor-1 in immunity and inflammation. *Curr. Opin. Immunol* 18:39-48.
35. Spies, B., H. Hochrein, M. Vabulas, K. Huster, D. H. Busch, F. Schmitz, A. Heit, and H. Wagner. 2003. Vaccination with plasmid DNA activates dendritic cells via Toll-like receptor 9 (TLR9) but functions in TLR9-deficient mice. *J. Immunol.* 171:5908-5912.
36. Hsu et al. 1996. Vaccination of Patients with B-Cell Lymphoma Using Autologous Antigen-Pulsed Dendritic Cells. *Nat. Med.* 2:52-58.
37. Paglia, et al. 1996. Murine Dendritic Cells Loaded In Vitro with Soluble Protein Prime Cytotoxic T Lymphocytes against Tumor Antigen In Vivo. *J. Exp. Med.* 1996, 183: 317-22.
38. Christensen and Shlomochik. 2007. Regulation of lupus-related autoantibody production and clinical disease by Toll-like receptors. *Semin. Immunol.* 19: 11-23.
39. Sweet et al. 2002. Colony-stimulating factor-1 suppresses responses to CpG DNA and expression of toll-like receptor 9 but enhances responses to lipopolysaccharide in murine macrophages. *J. Immunol.* 168: 392-99.
40. Xu et al., 2004. translation: Detection of FLT3 gene and FLT3/ITD gene mutation in chronic myeloid leukemia and its significance. *Ai Zheng*, 23:1218-21 [abstract available in English].
41. Hübel, et al., 2002. Therapeutic use of cytokines to modulate phagocyte function for the treatment of infections diseases: Current status of Granulocyte Colony-Stimulating Factor, Granulocyte-Macrophage Colony-Stimulating Factor, Macrophage Colony-Stimulating Factor, and Interferon-γ. *J. Infect. Dis.*, 185: 1490-501.
41. Fogg et al., 2006. A Clonogenic Bone Marrow Progenitor Specific for Macrophages and Dendritic Cells. *Science*, 311:83-87.
42. Takashima et al., 1995. Colony-stimulating Factor-1 Secreted by Fibroblasts Promotes the Growth of Dendritic Cell Lines XS Series) Derived From Murine Epidermis. *J. Immunol.*, 154:5128-35.

43. Chito and Stanley, 2006. Colony-stimulating Factor-1 in Immunity and Inflammation. *Curr. Op. Immunol.,* 28:39-48.
44. U.S. Pat. No. 7,198,948.
45. Stoll M L, Price K D, Silvin C J, Jiang F, Gavalchin J. 2007. Immunization with peptides derived from the idiotypic region of lupus-associated autoantibodies delays the development of lupus nephritis in the (SWR×NZB)F(1) murine model. *J Autoimmun.* (Epub ahead of print)
46. Zhang W, Frank M B, Reichlin M. 2002. Production and characterization of human monoclonal anti-idiotype antibodies to anti-dsDNA antibodies. *Lupus,* 11 (6):362-9.
47. Graf C, Heidel F, Tenzer S, Radsak M P, Solem F K, Britten C M, Huber C, Fischer T, Wolfel T. 2006. A neoepitope generated by a FLT3 internal tandem duplication (FLT3-ITD) is recognized by leukemia-reactive autologous CD8+ T cells. *Blood.* (Epub ahead of print).
48. Kappelmayer J, Udvardy M, Antal-Szalmas P. 2007. Pgp and FLT3: identification and modulation of two proteins that lead to chemotherapy resistance in acute myeloid leukemia. *Curr Med Chem.,* 14:519-30.
49. Zheng R, Small D. 2005. Mutant FLT3 signaling contributes to a block in myeloid differentiation. *Leuk Lymphoma.* 46:1679-87.
50. Advani A S. 2005. FLT3 and acute myelogenous leukemia: biology, clinical significance and therapeutic applications. *Curr Pharm Des.* 11:3449-57.

What is claimed is:

1. A method of increasing plasmacytoid dendritic cells (pDCs) in vitro, comprising:
   (A) culturing bone marrow cells comprising adherent and non-adherent cells;
   (B) quantitating the number of plasmacytoid dendritic cells (pDCs) within the bone marrow cells;
   (C) administering Macrophage-Colony Stimulating Factor (M-CSF) to the bone marrow cells;
   (D) quantitating the number of pDCs present after administration of M-CSF,
   wherein the number of pDCs after M-CSF administration is increased over the number of pDCs before administration of M-CSF.
2. The method of claim 1, wherein the number of pDCs is quantitated by measuring the level of at least one cell surface marker.
3. The method of claim 2, wherein the at least one cell surface marker is CD11c, CD45R, CD45RA, PDCA-1, CCR9, Ly49Q, Ly6C, Siglec-H, HLA-DR, CD4, CD123, BDCA-2, or BDCA-4.
4. The method of claim 1, further comprising quantitating the number of conventional dendritic cells (cDCs).
5. The method of claim 4, wherein the number of cDCs is quantitated by measuring the level of at least one cell surface marker.
6. The method of claim 1, wherein the M-CSF is administered in a Modified Vaccinia virus Ankara (MVA) viral vector.
7. The method of claim 1, further comprising stimulating the DCs by exposing them to at least one stimulatory agent.
8. The method of claim 7, wherein the at least one stimulatory agent is IFN-I, IL-6, IL-10, IL-12, TNF-α, a TLR-agonist, virus, bacteria, fungi, plant or parts thereof.

* * * * *